(12) United States Patent
Kanji

(10) Patent No.: US 7,008,629 B2
(45) Date of Patent: Mar. 7, 2006

(54) COMPOSITIONS COMPRISING AT LEAST ONE HETEROPOLYMER AND FIBERS, AND METHODS OF USING THE SAME

(75) Inventor: Mohamed Kanji, Edison, NJ (US)

(73) Assignee: L'Oréal S.A., Paris (FR)

( * ) Notice: Subject to any disclaimer, the term of this patent is extended or adjusted under 35 U.S.C. 154(b) by 0 days.

(21) Appl. No.: 10/198,931

(22) Filed: Jul. 22, 2002

(65) Prior Publication Data

US 2004/0013625 A1    Jan. 22, 2004

(51) Int. Cl.
*A61K 7/48*    (2006.01)

(52) U.S. Cl. .................... 424/401; 424/70.7; 424/78.37

(58) Field of Classification Search ................. 424/401, 424/70.1, 78, 37, 70.7, 62, 63
See application file for complete search history.

(56) References Cited

U.S. PATENT DOCUMENTS

| | | |
|---|---|---|
| 2,379,413 A | 7/1945 | Bradley |
| 2,450,940 A | 10/1948 | Cowan et al. |
| 2,463,264 A | 3/1949 | Graenacher |
| 2,662,068 A | 12/1953 | Floyd |
| 2,663,649 A | 12/1953 | Winkler |
| 2,890,097 A | 6/1959 | Coe |
| 2,962,461 A | 11/1960 | Toussaint et al. |
| 3,086,914 A | 4/1963 | Soloway ...................... 167/85 |
| 3,141,787 A | 7/1964 | Goetze et al. |
| 3,148,125 A | 9/1964 | Strianse et al. |
| 3,156,572 A | 11/1964 | Carlick et al. |
| 3,255,082 A | 6/1966 | Barton |
| 3,341,465 A | 9/1967 | Kaufman et al. |
| 3,412,115 A | 11/1968 | Floyd et al. |
| 3,615,289 A | 10/1971 | Felton |
| 3,645,705 A | 2/1972 | Miller et al. |
| 3,778,394 A | 12/1973 | Lovald et al. |
| 3,819,342 A | 6/1974 | Gunderman et al. |
| 3,857,960 A | 12/1974 | Mackles |
| 3,926,655 A | 12/1975 | Miles |
| 3,937,811 A | 2/1976 | Papantoniou et al. |
| 3,969,087 A | 7/1976 | Saito et al. |
| 4,049,792 A | 9/1977 | Elsnau |
| 4,051,159 A | 9/1977 | Tsoucalas et al. |
| 4,062,819 A | 12/1977 | Mains et al. |

(Continued)

FOREIGN PATENT DOCUMENTS

| | | |
|---|---|---|
| CA | 2003346 | 5/1990 |
| CA | 1319306 | 6/1993 |
| DE | 38 39 136 A1 | 5/1990 |
| DE | 38 43 892 A | 6/1990 |
| DE | 42 08 297 A | 9/1993 |
| DE | 42 34 886 A | 4/1994 |
| DE | 195 43 988 A | 5/1997 |
| DE | 197 07 309 A1 | 8/1998 |
| DE | 197 50 246 A1 | 5/1999 |
| DE | 199 51 010 A | 4/2001 |
| EP | 0 169 997 B1 | 2/1986 |
| EP | 0 295 886 B1 | 12/1988 |
| EP | 0 370 470 B1 | 5/1990 |
| EP | 0 374 332 A1 | 6/1990 |
| EP | 0 412 710 B1 | 2/1991 |
| EP | 0 444 633 A2 | 9/1991 |
| EP | 0 557 196 A1 | 8/1993 |
| EP | 0 602 905 B1 | 6/1994 |
| EP | 0 609 132 B1 | 8/1994 |
| EP | 0 623 670 A2 | 11/1994 |
| EP | 0 628 582 B1 | 12/1994 |
| EP | 0 673 642 B1 | 9/1995 |
| EP | 0 708 114 A1 | 4/1996 |
| EP | 0 749 746 A1 | 12/1996 |
| EP | 0 749 747 A1 | 12/1996 |

(Continued)

OTHER PUBLICATIONS

Bush Boake Allen, Inc., Uniclear Formulations, dated Oct. 13, 1998.
Certified English translation of FR 1 529 329.
Charles M. Hansen, "The Three Dimensional Solubility Parameter—Key to Paint Component Affinities: I. Solvents, Plasticizers, Polymers, and Resins," Journal of Paint Technology, vol. 39, No. 505, Feb. 1967, pp. 104–117.
English language DERWENT abstract of DE 42 08 297.
English language DERWENT abstract of DE 195 43 988.
English language DERWENT abstract of DE 197 07 309.
English language DERWENT abstract of DE 197 50 246.
English language DERWENT abstract of DE 199 51 010.
English language DERWENT abstract of DE 38 43 892.
English language DERWENT abstract of DE 38 39 136.
English language DERWENT abstract of DE 42 34 886.
English language DERWENT abstract of EP 0 169 997 B1.
English language DERWENT abstract of EP 0 557 196 A1.
English language DERWENT abstract of EP 0 609 132.
English language DERWENT abstract of EP 0 749 746 A1.
English language DERWENT abstract of EP 0 749 747 A1.
English language DERWENT abstract of EP 0 749 748.
English language DERWENT abstract of EP 0 775 483 A1.
English language DERWENT abstract of EP 0 820 764 A1.
English language DERWENT abstract of EP 0 847 752.
English language DERWENT abstract of EP 0 879 592 A2.
English language DERWENT abstract of EP 0 887 073 A1.
English language DERWENT abstract of EP 0 923 928 A1.

(Continued)

*Primary Examiner*—Jyothsna Venkat
(74) *Attorney, Agent, or Firm*—Finnegan, Henderson, Farabow, Garrett & Dunner L.L.P.

(57) ABSTRACT

Cosmetic compositions comprising at least one heteropolymer; fibers; and at least one compound chosen from at least one polysaccharide resin and at least one copolymer film former chosen from di-block, tri-block, multi-block, and radial copolymers; and methods for dispersing fibers in cosmetic compositions.

29 Claims, No Drawings]

U.S. PATENT DOCUMENTS

| | | |
|---|---|---|
| RE29,871 E | 12/1978 | Papantoniou et al. |
| 4,128,436 A | 12/1978 | O'Hara et al. |
| 4,137,306 A | 1/1979 | Rubino et al. |
| 4,148,875 A | 4/1979 | Barnett et al. |
| 4,150,002 A | 4/1979 | Drawert et al. |
| 4,275,054 A | 6/1981 | Sebag et al. |
| 4,275,055 A | 6/1981 | Nachtigal et al. ............ 424/70 |
| 4,278,658 A | 7/1981 | Hooper et al. |
| 4,279,658 A | 7/1981 | Harvey et al. |
| 4,337,298 A | 6/1982 | Karim et al. |
| 4,341,671 A | 7/1982 | Bolze et al. |
| 4,376,194 A | 3/1983 | Tanaka et al. |
| 4,387,090 A | 6/1983 | Bolich, Jr. ................ 424/70 |
| 4,438,240 A | 3/1984 | Tanaka et al. |
| 4,466,936 A | 8/1984 | Schapel |
| 4,536,405 A | 8/1985 | Nara et al. |
| 4,552,693 A | 11/1985 | Hussain et al. ............ 252/522 |
| 4,571,267 A | 2/1986 | Drawert et al. |
| 4,620,492 A | 11/1986 | Vogg et al. |
| 4,655,836 A | 4/1987 | Drawert et al. |
| 4,663,428 A | 5/1987 | Okitu et al. |
| 4,699,779 A | 10/1987 | Palinczar |
| 4,712,571 A | 12/1987 | Remz et al. |
| 4,769,285 A | 9/1988 | Rasmussen |
| 4,806,338 A | 2/1989 | Smith ......................... 424/47 |
| 4,806,345 A | 2/1989 | Bhattacharyya ............ 424/70 |
| 4,820,765 A | 4/1989 | Whyzmuzis |
| 4,822,601 A | 4/1989 | Goode et al. |
| 4,871,536 A | 10/1989 | Arraudeau et al. .......... 424/59 |
| 4,937,069 A | 6/1990 | Shin |
| 4,952,245 A | 8/1990 | Iwano et al. |
| 5,034,219 A | 7/1991 | Deshpande et al. |
| 5,061,289 A | 10/1991 | Clausen et al. |
| 5,069,897 A | 12/1991 | Orr ........................... 424/66 |
| 5,073,364 A | 12/1991 | Giezendanner et al. |
| 5,085,859 A | 2/1992 | Halloran et al. |
| 5,102,656 A | 4/1992 | Kasat |
| 5,186,318 A | 2/1993 | Oestreich et al. ............ 206/37 |
| 5,196,260 A | 3/1993 | Dirschl et al. |
| 5,214,326 A | 5/1993 | Yonei |
| 5,223,559 A | 6/1993 | Arraudeau et al. |
| 5,268,029 A | 12/1993 | Demangeon et al. |
| 5,272,241 A | 12/1993 | Lucarelli et al. ............ 528/15 |
| 5,290,555 A | 3/1994 | Guthauser et al. |
| 5,302,398 A | 4/1994 | Egidio et al. |
| 5,342,894 A | 8/1994 | Robeson et al. |
| 5,362,482 A | 11/1994 | Yoneyama et al. |
| 5,372,852 A | 12/1994 | Titterington et al. |
| 5,389,363 A | 2/1995 | Snyder et al. |
| 5,472,686 A | 12/1995 | Tsubaki et al. |
| 5,486,431 A | 1/1996 | Tuttle et al. |
| 5,489,431 A | 2/1996 | Ascione et al. |
| 5,500,209 A | 3/1996 | Mendolia et al. |
| 5,505,937 A | 4/1996 | Castrogiovanni et al. |
| 5,510,452 A | 4/1996 | Santhanam ................ 528/291 |
| 5,536,871 A | 7/1996 | Santhanam ................ 560/196 |
| 5,538,718 A | 7/1996 | Aul et al. |
| 5,538,793 A | 7/1996 | Inokuchi et al. |
| 5,540,853 A | 7/1996 | Trinh et al. ................ 510/101 |
| 5,603,925 A | 2/1997 | Ross et al. .................. 424/65 |
| 5,605,651 A | 2/1997 | Balzer |
| 5,610,199 A | 3/1997 | Cohen et al. |
| 5,612,043 A | 3/1997 | Deprez et al. |
| 5,616,331 A | 4/1997 | Allard et al. |
| 5,618,523 A | 4/1997 | Zysman et al. |
| 5,620,693 A | 4/1997 | Piot et al. |
| 5,628,029 A | 5/1997 | Evoy |
| 5,645,632 A | 7/1997 | Pavlin |
| 5,667,770 A | 9/1997 | Szweda et al. ............. 424/64 |
| 5,679,357 A | 10/1997 | Dubief et al. .............. 424/401 |
| 5,683,817 A | 11/1997 | Kenmochi |
| 5,702,519 A | 12/1997 | Nitta et al. |
| 5,719,255 A | 2/1998 | Heucher et al. |
| 5,747,625 A | 5/1998 | Furukawa et al. |
| 5,750,125 A | 5/1998 | Lahanas et al. |
| 5,750,127 A | 5/1998 | Rokitowski |
| 5,750,489 A | 5/1998 | Garcia et al. |
| 5,769,902 A | 6/1998 | Samain |
| 5,780,517 A | 7/1998 | Cohen et al. |
| 5,783,657 A | 7/1998 | Pavlin et al. |
| 5,800,816 A | 9/1998 | Brieva et al. ............... 424/63 |
| 5,807,968 A | 9/1998 | Heinrich et al. |
| 5,830,444 A | 11/1998 | Miguel |
| 5,830,483 A | 11/1998 | Seidel et al. |
| 5,837,223 A | 11/1998 | Barone et al. |
| 5,849,275 A | 12/1998 | Calello et al. |
| 5,849,278 A | 12/1998 | Piot et al. |
| 5,849,333 A | 12/1998 | Nordhauser et al. |
| 5,851,517 A | 12/1998 | Mougin et al. |
| 5,857,903 A | 1/1999 | Ramspeck et al. |
| 5,858,338 A | 1/1999 | Piot et al. |
| 5,866,149 A | 2/1999 | Piot et al. |
| 5,871,764 A | 2/1999 | Diaz et al. |
| 5,874,069 A | 2/1999 | Mendolia et al. ........... 424/65 |
| 5,882,363 A | 3/1999 | Spaulding et al. |
| 5,891,424 A | 4/1999 | Bretzler et al. |
| 5,897,869 A | 4/1999 | Roulier et al. ............. 424/401 |
| 5,902,592 A | 5/1999 | Bara et al. |
| 5,908,631 A | 6/1999 | Arnaud et al. |
| 5,911,974 A | 6/1999 | Brieva et al. ............... 424/64 |
| 5,919,441 A | 7/1999 | Mendolia et al. ......... 424/78.08 |
| 5,925,337 A | 7/1999 | Arraudeau et al. |
| 5,945,095 A | 8/1999 | Mougin et al. |
| 5,945,112 A | 8/1999 | Flynn et al. |
| 5,959,009 A | 9/1999 | Konik et al. ............... 524/261 |
| 5,961,998 A | 10/1999 | Arnaud et al. |
| 5,965,112 A | 10/1999 | Brieva et al. ............... 424/64 |
| 5,972,095 A | 10/1999 | Graves et al. |
| 5,972,354 A | 10/1999 | de la Poterie et al. |
| 5,972,359 A | 10/1999 | Sine et al. |
| 5,976,514 A | 11/1999 | Guskey et al. |
| 5,981,680 A | 11/1999 | Petroff et al. |
| 5,985,298 A | 11/1999 | Brieva et al. |
| 5,993,787 A | 11/1999 | Sun et al. |
| 5,998,570 A | 12/1999 | Pavlin et al. |
| 6,001,980 A | 12/1999 | Borzo et al. |
| 6,004,567 A | 12/1999 | Marchi-Lemann et al. |
| 6,007,799 A | 12/1999 | Lee et al. |
| 6,019,962 A | 2/2000 | Rabe et al. |
| 6,036,947 A | 3/2000 | Barone et al. |
| 6,045,782 A | 4/2000 | Krog et al. |
| 6,045,823 A | 4/2000 | Vollhardt et al. |
| 6,051,216 A | 4/2000 | Barr et al. ............... 424/78.35 |
| 6,054,517 A | 4/2000 | Spaulding et al. |
| 6,060,072 A | 5/2000 | Konik et al. ............... 424/401 |
| 6,063,398 A | 5/2000 | Gueret |
| 6,066,328 A | 5/2000 | Ribier et al. |
| 6,074,654 A | 6/2000 | Drechsler et al. ........... 424/401 |
| 6,103,249 A | 8/2000 | Roulier et al. ............. 424/401 |
| 6,106,820 A | 8/2000 | Morrissey et al. |
| 6,111,055 A | 8/2000 | Berger et al. |
| 6,156,325 A | 12/2000 | Farer et al. ............... 424/401 |
| 6,156,804 A | 12/2000 | Chevalier et al. |
| 6,165,454 A | 12/2000 | Patel et al. |
| 6,165,971 A | 12/2000 | Oppenlander et al. |
| 6,171,347 B1 | 1/2001 | Kunz |
| 6,177,523 B1 | 1/2001 | Reich et al. ............... 525/459 |
| 6,180,117 B1 | 1/2001 | Berthiaume et al. |
| 6,180,123 B1 | 1/2001 | Mondet |
| 6,190,673 B1 | 2/2001 | Guskey et al. ............. 424/401 |
| 6,197,100 B1 | 3/2001 | Melbouci |

| | | | | | | |
|---|---|---|---|---|---|---|
| 6,203,780 B1 | 3/2001 | Arnaud et al. | | EP | 0 958 805 A2 | 11/1999 |
| 6,203,807 B1 | 3/2001 | Lemann | | EP | 0 958 811 A1 | 11/1999 |
| 6,214,329 B1 | 4/2001 | Brieva et al. | | EP | 0 959 066 A2 | 11/1999 |
| 6,221,389 B1 | 4/2001 | Cannell et al. | | EP | 0 959 091 A1 | 11/1999 |
| 6,224,851 B1 | 5/2001 | Bara | | EP | 0 976 390 A1 | 2/2000 |
| 6,242,509 B1 | 6/2001 | Berger et al. | | EP | 0 984 025 A2 | 3/2000 |
| 6,251,375 B1 | 6/2001 | Bara | | EP | 1 002 514 A1 | 5/2000 |
| 6,251,409 B1 | 6/2001 | Hegyi et al. | | EP | 1 031 342 A1 | 8/2000 |
| 6,254,876 B1 | 7/2001 | de la Poterie et al. | | EP | 1 048 282 A1 | 11/2000 |
| 6,254,877 B1 | 7/2001 | de la Poterie et al. | | EP | 1 053 742 A1 | 11/2000 |
| 6,264,933 B1 | 7/2001 | Bodelin et al. | | EP | 1 062 944 A1 | 12/2000 |
| 6,268,466 B1 | 7/2001 | MacQueen et al. | | EP | 1 062 959 A1 | 12/2000 |
| 6,280,846 B1 | 8/2001 | Darby et al. | | EP | 1 064 919 A1 | 1/2001 |
| 6,287,552 B1 | 9/2001 | Tournilhac et al. | | EP | 1 064 920 A1 | 1/2001 |
| 6,325,994 B1 | 12/2001 | Collin et al. | | EP | 1 066 814 A1 | 1/2001 |
| 6,348,563 B1 | 2/2002 | Fukuda et al. | | EP | 1 068 854 A1 | 1/2001 |
| 6,372,235 B1 | 4/2002 | Livoreil et al. | | EP | 1 068 855 A1 | 1/2001 |
| 6,376,078 B1 | 4/2002 | Inokuchi | | EP | 1 068 856 A1 | 1/2001 |
| 6,383,502 B1 | 5/2002 | Dunshee et al. | | EP | 1 086 945 A1 | 3/2001 |
| 6,399,080 B1 | 6/2002 | Bara | | EP | 1 090 627 B1 | 4/2001 |
| 6,399,081 B1 | 6/2002 | Nakanishi et al. | | EP | 1 095 959 A2 | 5/2001 |
| 6,402,408 B1 * | 6/2002 | Ferrari ........................ 401/64 | | EP | 1 114 636 A1 | 7/2001 |
| 6,423,306 B1 | 7/2002 | Caes et al. | | EP | 1 213 011 A1 | 6/2002 |
| 6,423,324 B1 | 7/2002 | Murphy et al. | | EP | 1 213 316 A2 | 6/2002 |
| 6,428,773 B1 | 8/2002 | Oko et al. | | FR | 1 529 329 | 5/1968 |
| 6,432,391 B1 | 8/2002 | Bara | | FR | 2 232 303 | 1/1975 |
| 6,447,759 B1 | 9/2002 | Noguchi et al. | | FR | 2 674 126 | 9/1992 |
| 6,469,131 B1 | 10/2002 | Lawson et al. | | FR | 2 785 179 | 5/2000 |
| 6,475,500 B1 | 11/2002 | Vatter et al. | | FR | 2 796 270 | 1/2001 |
| 6,479,686 B1 | 11/2002 | Nakanishi et al. | | FR | 2 796 271 | 1/2001 |
| 6,482,400 B1 | 11/2002 | Collin | | FR | 2 796 272 | 1/2001 |
| 6,491,931 B1 | 12/2002 | Collin | | FR | 2 796 273 | 1/2001 |
| 6,497,861 B1 | 12/2002 | Wang et al. | | FR | 2 796 276 | 1/2001 |
| 6,506,716 B1 | 1/2003 | Delplancke et al. | | FR | 2 802 806 | 6/2001 |
| 6,649,173 B1 | 11/2003 | Arnaud et al. | | FR | 2 804 017 | 7/2001 |
| 6,682,748 B1 | 1/2004 | De La Poterie et al. | | FR | 2 804 018 | 7/2001 |
| 6,726,917 B1 * | 4/2004 | Kanji et al. ................ 424/401 | | FR | 2 810 562 | 12/2001 |
| 6,749,173 B1 | 6/2004 | Heiling | | FR | 2 811 225 | 1/2002 |
| 6,761,881 B1 | 7/2004 | Bara | | FR | 2 811 552 | 1/2002 |
| 6,875,245 B1 | 4/2005 | Pavlin | | FR | 2 816 506 | 5/2002 |
| 2003/0086883 A1 | 5/2003 | Feng et al. | | FR | 2 817 739 | 6/2002 |
| 2003/0147837 A1 | 8/2003 | Cavazzuti et al. | | FR | 2 817 740 | 6/2002 |
| 2003/0161807 A1 | 8/2003 | Lemann | | FR | 2 817 743 | 6/2002 |
| 2003/0161848 A1 | 8/2003 | Ferrari et al. | | FR | 2 819 399 | 7/2002 |
| 2003/0185780 A1 | 10/2003 | Ferrari et al. | | FR | 2 819 400 | 7/2002 |
| 2003/0198613 A1 | 10/2003 | Feng et al. | | FR | 2 819 402 | 7/2002 |
| 2004/0013625 A1 | 1/2004 | Kanji | | GB | 1 117 129 | 6/1968 |
| 2004/0028636 A1 | 2/2004 | Collin | | GB | 1 194 901 | 6/1970 |
| 2004/0042980 A1 | 3/2004 | Kanji et al. | | GB | 1 194 902 | 6/1970 |
| 2004/0086478 A1 | 5/2004 | Ferrari | | GB | 1 220 069 | 1/1971 |
| 2004/0091510 A1 | 5/2004 | Feng et al. | | GB | 1 273 004 | 5/1972 |
| 2004/0126401 A1 | 7/2004 | Collin | | GB | 1 444 204 | 7/1976 |
| 2004/0166076 A1 | 8/2004 | Ferrari et al. | | GB | 2 014 852 | 9/1979 |
| 2004/0166133 A1 | 8/2004 | Cavazzuti et al. | | GB | 2 021 411 A | 12/1979 |
| | | | | GB | 2 147 305 A | 5/1985 |
| FOREIGN PATENT DOCUMENTS | | | | GB | 2 196 978 A | 5/1988 |
| EP | | 0 749 748 A | 12/1996 | JP | 50/58242 | 5/1975 |
| EP | | 0 775 483 A1 | 5/1997 | JP | 53/043577 | 4/1978 |
| EP | | 0 797 976 A2 | 10/1997 | JP | 56/123909 | 9/1981 |
| EP | | 0 820 764 A1 | 1/1998 | JP | 56/166276 | 12/1981 |
| EP | | 0 847 752 A1 | 6/1998 | JP | 61/065809 | 4/1986 |
| EP | | 0 877 063 B1 | 11/1998 | JP | 62/061911 | 3/1987 |
| EP | | 0 879 592 A2 | 11/1998 | JP | 2/127568 | 5/1990 |
| EP | | 0 887 073 A1 | 12/1998 | JP | 02/200612 | 8/1990 |
| EP | | 0 923 928 A1 | 6/1999 | JP | 2/216279 | 8/1990 |
| EP | | 0 925 780 A1 | 6/1999 | JP | 3/014683 | 1/1991 |
| EP | | 0 928 608 A2 | 7/1999 | JP | 04/346909 | 12/1992 |
| EP | | 0 930 058 B1 | 7/1999 | JP | 7/179795 | 7/1995 |
| EP | | 0 930 060 A1 | 7/1999 | JP | 7/267827 | 10/1995 |
| EP | | 0 943 340 A1 | 9/1999 | JP | 8/225316 | 9/1996 |
| EP | | 0 958 804 A2 | 11/1999 | JP | 9/20631 | 1/1997 |

| | | |
|---|---|---|
| JP | 09/255560 | 9/1997 |
| JP | 9/295922 | 11/1997 |
| JP | 10/007527 | 1/1998 |
| JP | 10/120903 | 5/1998 |
| JP | 10/212213 | 8/1998 |
| JP | 10/259344 | 9/1998 |
| JP | 11/106216 | 4/1999 |
| JP | 11/335228 | 12/1999 |
| JP | 11/335242 | 12/1999 |
| JP | 11/335254 | 12/1999 |
| JP | 2000038314 A | 2/2000 |
| JP | 2000038316 A | 2/2000 |
| JP | 2000038317 A | 2/2000 |
| JP | 2000038321 A | 2/2000 |
| JP | 2000086427 A | 3/2000 |
| JP | 2000086429 A | 3/2000 |
| JP | 2000086438 A | 3/2000 |
| WO | WO 86/04916 | 8/1986 |
| WO | WO 87/03783 | 7/1987 |
| WO | WO 91/12793 | 9/1991 |
| WO | WO 93/21763 | 11/1993 |
| WO | WO 93/23008 | 11/1993 |
| WO | WO 94/18261 | 8/1994 |
| WO | WO 94/21233 | 9/1994 |
| WO | WO 95/15741 | 6/1995 |
| WO | WO 95/24887 | 9/1995 |
| WO | WO 95/33000 | 12/1995 |
| WO | WO 96/15761 | 5/1996 |
| WO | WO 96/40044 | 12/1996 |
| WO | WO 97/17057 | 5/1997 |
| WO | WO 97/36573 | 10/1997 |
| WO | WO 98/17243 | 4/1998 |
| WO | WO 98/17705 | 4/1998 |
| WO | WO 98/22078 | 5/1998 |
| WO | WO 98/27162 | 6/1998 |
| WO | WO 98/42298 | 10/1998 |
| WO | WO 98/47470 | 10/1998 |
| WO | WO 98/52534 | 11/1998 |
| WO | WO 98/58623 | 12/1998 |
| WO | WO 99/24002 | 5/1999 |
| WO | WO 00/27350 | 5/2000 |
| WO | WO 00/40216 | 7/2000 |
| WO | WO 00/61080 | 10/2000 |
| WO | WO 00/61081 | 10/2000 |
| WO | WO 00/74519 A2 | 12/2000 |
| WO | WO 01/51020 A1 | 7/2001 |
| WO | WO 01/52799 A1 | 7/2001 |
| WO | WO 01/97758 A2 | 12/2001 |
| WO | WO 01/97773 A1 | 12/2001 |
| WO | WO 02/03932 A2 | 1/2002 |
| WO | WO 02/03935 A2 | 1/2002 |
| WO | WO 02/03950 A2 | 1/2002 |
| WO | WO 02/03951 A2 | 1/2002 |
| WO | WO 02/47605 A2 | 6/2002 |
| WO | WO 02/47608 A2 | 6/2002 |
| WO | WO 02/47619 A2 | 6/2002 |
| WO | WO 02/47620 A2 | 6/2002 |
| WO | WO 02/47622 A2 | 6/2002 |
| WO | WO 02/47627 A1 | 6/2002 |
| WO | WO 02/47629 A1 | 6/2002 |
| WO | WO 02/47630 A1 | 6/2002 |
| WO | WO 02/47658 A2 | 6/2002 |
| WO | WO 02/49583 A1 | 6/2002 |
| WO | WO 02/49601 A1 | 6/2002 |
| WO | WO 02/055030 A2 | 7/2002 |
| WO | WO 02/055031 A1 | 7/2002 |
| WO | WO 02/056845 A1 | 7/2002 |
| WO | WO 02/056847 A1 | 7/2002 |
| WO | WO 02/056848 A1 | 7/2002 |
| WO | WO 02/092047 A1 | 11/2002 |
| WO | WO 02/092663 A1 | 11/2002 |
| WO | WO 02/102322 A2 | 12/2002 |

OTHER PUBLICATIONS

English language DERWENT abstract of EP 0 925 780 A1.
English language DERWENT abstract of EP 0 930 058 B1.
English language DERWENT abstract of EP 0 930 060 A1.
English language DERWENT abstract of EP 0 943 340 A1.
English language DERWENT abstract of EP 0 958 811 A1.
English language DERWENT abstract of EP 0 959 066 A2.
English language DERWENT abstract of EP 0 959 091 A1.
English language DERWENT abstract of EP 0 976 390 A1.
English language DERWENT abstract of EP 0 984 025 A2.
English language DERWENT abstract of EP 1 002 514.
English language DERWENT abstract of EP 1 031 342 A1.
English language DERWENT abstract of EP 1 048 282 A1.
English language DERWENT abstract of EP 1 053 742.
English language DERWENT abstract of EP 1 064 919.
English language DERWENT abstract of EP 1 064 920.
English language DERWENT abstract of EP 1 066 814.
English language DERWENT abstract of EP 1 068 854 A1.
English language DERWENT abstract of EP 1 068 855 A1.
English language DERWENT abstract of EP 1 068 856 A1.
English language DERWENT abstract of EP 1 086 945 A1.
English language DERWENT abstract of EP 1 090 627 B1.
English language DERWENT abstract of EP 1 114 636 A1.
English language DERWENT abstract of FR 2 232 303.
English language DERWENT abstract of FR 2 674 126.
English language DERWENT abstract of FR 2 785 179.
English language DERWENT abstract of FR 2 796 270.
English language DERWENT abstract of FR 2 796 271.
English language DERWENT abstract of FR 2 796 272.
English language DERWENT abstract of FR 2 796 273.
English language DERWENT abstract of FR 2 796 276.
English language DERWENT abstract of FR 2 802 806.
English language DERWENT abstract of FR 2 804 017.
Enlgish language DERWENT abstract of FR 2 804 018.
English language DERWENT abstract of FR 2 810 562.
English language DERWENT abstract of FR 2 811 225.
English language DERWENT abstract of FR 2 811 552.
English language DERWENT abstract of FR 2 816 506.
English language DERWENT abstract of FR 2 817 739.
English language DERWENT abstract of FR 2 817 740.
English language DERWENT abstract of FR 2 817 743.
English language DERWENT abstract of FR 2 819 399.
English language DERWENT abstract of FR 2 819 400.
English language DERWENT abstract of FR 2 819 402.
English language DERWENT abstract of JP 02/200612.
English language DERWENT abstract of JP 04/346909.
English language DERWENT abstract of JP 09/255560.
English language DERWENT abstract of JP 10/007527.
English language DERWENT abstract of JP 10/120903.
English language DERWENT abstract of JP 10/212213.
English language DERWENT abstract of JP 10/259344.
English language DERWENT abstract of JP 11/106216.
English language DERWENT abstract of JP 11/335228.
English language DERWENT abstract of JP 11/335242.
English language DERWENT abstract of JP 11/335254.
English language DERWENT abstract of JP 2000038314 A.
English language DERWENT abstract of JP 2000038316 A and JP 2000038317 A.
English language DERWENT abstract of JP 2000038321 A.
English language DERWENT abstract of JP 2000086427 A.
English language DERWENT abstract of JP 2000086429 A.
English language DERWENT abstract of JP 2000086438 A.

English language DERWENT abstract of JP 2127568.
English language DERWENT abstract of JP 2216279.
English language DERWENT abstract of JP 3014683.
English language DERWENT abstract of JP 7179795.
English language DERWENT abstract of JP 7267827.
English language DERWENT abstract of JP 8225316.
English language DERWENT abstract of JP 920631.
English language DERWENT abstract of JP 9295922.
English language DERWENT abstract of JP 62061911.
English language abstract of JP 53043577 from Patent Abstracts of Japan.
English language abstract of JP 56123909 from Patent Abstracts of Japan.
English language abstract of JP 56166276 from Patent Abstracts of Japan.
English language abstract of JP 61065809 from Patent Abstracts of Japan.
Enlgish language DERWENT abstract of WO 02/055031 A1.
English language DERWENT abstract of WO 02/056845 A1.
French Search Report in FR 0000920 (priority document for PCT/FR01/00229, dated Nov. 10, 2000.
French Search Report in FR 0001004 (priority document), dated Nov. 10, 2000.
French Search Report in FR 0008084 (priority document), dated Mar. 28, 2001.
French Search Report in FR 0008913 (priority document), dated Mar. 20, 2001.
French Search Report in FR 0016161 (priority document), dated Sep. 6, 2001.
French Search Report in FR 0016163 (priority document), dated Aug. 1, 2001.
French Search Report in FR 0016164 (priority document), dated Sep. 6, 2001.
French Search Report in FR 0016180 (priority document), dated Oct. 16, 2001.
French Search Report in FR 0100479, dated Sep. 17, 2001.
French Search Report in FR 0100620, dated Nov. 6, 2001.
French Search Report in FR 0100623 (priority document ), dated Oct. 9, 2001.
French Search Report in FR 0114529, dated Aug. 26, 2002.
French Search Report in FR 0114530, dated Aug. 26, 2002.
French Search Report in FR 9909176 (priority document), dated Mar. 23, 2000.
French Search Report in FR 9909177 (priority document), dated Mar. 30, 2000.
French Search Report in FR 9916588 (priority document), dated Oct. 16, 2000.
Handbook of Cosmetic Science and Tech. Elsevier Advanced Tech., 1st Edition (1994), p. 19.
International Search Report in PCT/FR01/00229 (the priority document), dated Apr. 18, 2001.
International Search Report in PCT/FR01/01958 (priority document), dated Oct. 26, 2001.
International Search Report in PCT/FR01/03726, dated Apr. 18, 2002.
International Search Report in PCT/FR01/03937 (priority document), dated Apr. 23, 2002.
International Search Report in PCT/FR01/03938 (priority document), dated Jun. 10, 2002.
International Search Report in PCT/FR01/03939 (priority document for FR 0016164), dated Apr. 15, 2002.
International Search Report in PCT/FR01/03940 (priority document for FR 0016161), dated Mar. 13, 2002.
International Search Report in PCT/FR01/03945 (priority document for FR 0016163), dated May 31, 2002.
International Search Report in PCT/FR02/00129, dated Jun. 14, 2002.
International Search Report in PCT/FR02/00144 (priority document for FR 0100479), dated Jun. 14, 2002.
International Search Report in PCT/FR02/00194, dated Jun. 12, 2002.
International Search Report in PCT/IB00/02000, dated Aug. 8, 2001.
International Search Report in PCT/IB00/02002, dated Sep. 4, 2001.
International Search Report in PCT/IB00/02006, dated Aug. 8, 2001.
International Search Report in PCT/IB01/02780, dated Apr. 10, 2002.
International Search Report in PCT/IB01/02786, dated Oct. 2, 2002.
International Search Report in PCT/IB01/02820, dated May 27, 2002.
International Search Report in PCT/IB01/02833, dated May 24, 2002.
International Search Report in PCT/IB01/02840, dated Jun. 11, 2002.
International Search Report in PCT/US 00/33596, dated Aug. 8, 2001.
International Search Report in PCT/US 01/47454, dated Aug. 29, 2002.
International Search Report in PCT/US 01/47459, dated Feb. 6, 2003.
International Search Report in PCT/US 01/47496, dated Feb. 26, 2003.
International Search Report in PCT/US 01/47497, dated Dec. 2, 2002.
International Search Report in PCT/US 01/47499, dated Aug. 8, 2002.
Kenji Hanabusa et al., Easy Preparation and Prominent Gelation of New Gelator Based on L–Lysine, 2000 Chem. Letters, 1070–1071.
Kenji Hanabusa et al., Prominent Gelation and Chiral Aggregation of Alkylamides Derived from trans–1,2–Diaminocyclohexane, Angew. Chem. Int. Ed. Engl. 1996, 35, No. 17, 1949–1951.
Kenji Hanabusa et al., Terephthaloyl Derivatives as New Gelators; Excellent Gelation Ability and Remarkable Increase of Gel Strength by Adding Polymers, 1999 Chemistry Letters 767–768.
Kirk–Othmer, "Encyclopedia of Chemical Technology", Third Edition, vol. 22, John Wiley & Sons, 1983, pp. 332–342.
Milan Jokic et al., A Novel Type of Small Organic Gelators: Bis(Amino Acid) Oxalyl Amides, 1995 J. Chem. Soc., Chem. Commun., 1723–1724.
P. Terech, "Low–Molecular Weight Organogelators," in Specialist Surfactants, ch. 8, pp. 208–268 (I.D. Robb, ed., 1997).
Partial International Search Report in PCT/US 01/47497, dated Nov. 15, 2002.
Toshimi Shimizu et al., Stereochemical Effect of Even–Odd Connecting Links on Supramolecular Assemblies Made of 1–Glucosamide Bolaamphiphiles, J. Am Chem. Soc. 1997, 119, 2812–2818.

Xuzhong Luo et al., Self–assembled organogels formed by monoalkyl derivatives of oxamide, 2000 Chem. Commun. 2091–92.

Yasuda et al., Novel Low–molecular–weight Organic Gels: N,N', N"–Tristearyltrimesamide/Organic Solvent System, Chemistry Letters, pp. 575–576, 1996, the month of publication is not available.

PCT Application No. PCT/FR01/03963; Title: Cosmetic Compositions Containing at Least One Heteropolymer and at Least One Gelling Agent and Methods of Using the Same Inventor: Véronique Ferrari International Filing Date: Dec. 12, 2001.

PCT Application No. PCT/FR01/03965; Title: Cosmetic Composition Comprising Hetero Polymers and a Solid Substance and Method of Using Same Inventors: Roberto Cavazzuti et al. International Filing Date: Dec. 12, 2001.

PCT Application No. PCT/IB00/02000; Title: Composition Comprising at Least One Hetero Polymer and at Least One Inert Filler and Methods for Use Inventors: Véronique Ferrari et al. International Filing Date: Dec. 12, 2000.

PCT Application No. PCT/IB00/02006; Title: Cosmetic Compositions Containing at Least One Heteropolymer and at Least One Gelling Agent and Methods of Using the Same Inventor: Véronique Ferrari International Filing Date:Dec. 12, 2000.

PCT Application No. PCT/IB01/02780; Title: Composition Structured with a Polymer Containing a Heteroatom and Organogelator International Filing Date: Dec. 12, 2001.

PCT Application No. PCT/US00/33596; Title Cosmetic Composition Comprising Hetero Polymers and a Solid Substance and Method of Using Same Inventors: Roberto Cavazzuti et al. International Filing Date: Dec. 12, 2000.

PCT Application No. PCT/US01/47454; Title: Compositions Containing Heteropolymers and Oil–Soluble Polymers and Methods of Using Same Inventors: Carlos Pinzon and Paul Thau U.S. Filing Date: Dec. 12, 2001.

PCT Application No. PCT/US01/47459; Title: Cosmetic Compositions Containing at Least One Hetero Polymer and at Least One Film–Forming Silicone Resin and Methods of Using Inventors: Mohamed Kanji et al. U.S. Filing Date:Dec. 12, 2001.

PCT Application No. PCT/US01/47496; Title: Compositions Containing Heteropolymers and Methods of Using Same Inventors: Carlos Pinzon and Paul Thau U.S. Filing Date: Dec. 12, 2001.

PCT Application No. PCT/US01/47497; Title: Compositions Containing Heteropolymers and Oil–Soluble Esters and Methods of Using Same Inventors: Carlos Pinzon and Paul Thau U.S. Filing Date: Dec. 12, 2001.

PCT Application No. PCT/US01/47499; Title: Cosmetic Compositions Containing Heteropolymers and Oil–Soluble Cationic Surfactants and Methods of Using Same Inventors: Carlos Pinzon and Paul Thau U.S. Filing Date: Dec. 12, 2001.

PCT Application No. PCT/US03/41618; Title: Cosmetic Compositions Comprising a Structuring Agent, Silicone Powder and Swelling Agent Inventor: Shao Xiang Lu, Terry Van Liew, Nathalie Geffroy–Hyland International Filing Date: Dec. 22, 2003.

PCT Application No. PCT/US04/01071; Title: Long Wear Cosmetic Composition Inventor: Balanda Atis International Filing Date: Jan. 16, 2004.

U.S. District Court for the District of New Jersey Civil Docket for *L'Oreal S.A. v. Estee Lauder Companies, Inc.*, Civ. No. 04–1660 (HAA) (D.N.J. filed Apr. 4, 2004) (retrieved Jan. 2, 2005).

Estee Lauder's Response to Plaintiffs' First Set of Interrogatories (Nos. 1–6) in *L'Oreal S.A. v. Estee Lauder Companies, Inc.*, Civ. No. 04–1660 (HAA) (D.N.J. filed Apr. 4, 2004).

1993 McCutcheon's vol. 1: Emulsifiers & Detergents North American and International Editions, MC Publishing Co., Glen Rock NJ (1993), pp. 272–273.

English language abstract of JP 50/58242.

English language DERWENT abstrct of WO 01/97773.

English language DERWENT abstract of WO 02/056847.

English language DERWENT abstract of WO 02/056848.

English language DERWENT abstract of WO 02/47622.

English language DERWENT abstract of WO 02/47629.

English language DERWENT abstract of WO 02/47630.

English language DERWENT abstract of WO 86/04916.

Origins Full Story ™ Lush lash mascara product packaging, believed to have first been sold in 2003.

Estee Lauder MagnaScopic Maximum Volume mascara product packaging, believed to have first been sold in 2003.

International Search Report in PCT/US04/01071, dated Feb. 22, 2005.

International Search Report in PCT/US03/41618, dated Mar. 11, 2005.

* cited by examiner

COMPOSITIONS COMPRISING AT LEAST ONE HETEROPOLYMER AND FIBERS, AND METHODS OF USING THE SAME

The present invention relates to compositions and methods of dispersing fibers in a cosmetic composition comprising including in the composition at least one heteropolymer and fibers, wherein the at least one heteropolymer is present in an amount effective to disperse the fibers.

The use of fibers in mascara compositions to lengthen or volumize eyelashes is known in the art. However, the inclusion of fibers in these compositions has presented various possible difficulties. One problem that is prevalent in the preparation of formulations in the cosmetic industry is the dispersion of components which make up the composition. A great deal of time and energy is spent in an attempt to obtain an even distribution or dispersion of ingredients. A uniform dispersion of components that make up a cosmetic or pharmaceutical composition, including dispersion of pigments, can result in enhanced properties such as improved efficacy, higher gloss, uniformity of batches, less clumping, and less energy required for mixing.

Another possible drawbacks of fiber use has been undesirable flaking and detachment of the fibers from the eyelashes that may occur due to the insufficient adhesive properties of the film formers in the mascara. Such flaking also may make it difficult to apply more than one coat of mascara, as the application of subsequent coats may further act to detach fibers from the lashes.

Further, many cosmetic products comprise a structured, i.e., gelled and/or rigidified, liquid fatty phase, such as, for example, in mascaras, lipsticks, concealer products, eyeshadows, and foundations. This structuring may be obtained with the aid of traditional waxes and/or fillers. Unfortunately, these waxes and fillers may have a tendency to make the composition matte, as do fibers, which may not always be desirable, in particular for a mascara. Specifically, consumers are always on the lookout for a mascara which can deposit a film which appears to enhance the volume and/or length of eyelashes and which is also increasingly glossy.

The tendency to flake and the gloss of a cosmetic composition comprising fibers may be associated with the nature of the liquid fatty phase. The liquid fatty phase of mascaras commonly comprise a traditional wax. As discussed above, traditional waxes in cosmetic compositions generally results in a composition having a dull and matte look. Further, traditional waxes may not effectively disperse fibers in the composition, thus resulting in clumping, and therefore, increased flaking and detachment of the fibers from eyelashes.

Accordingly, there existed a need in the art to find a way to use fibers to obtain enhanced volume and/or length for eyelashes in a cosmetic composition without the disadvantages of flaking and detachment of the fibers and without the dulling effect of traditional waxes and of the fibers themselves. It was also desired to use fibers but also obtain ease of application. Development of such compositions involves a difficult balance, as at least one component used in a fiber-containing cosmetic composition, particularly for use on eyelashes, should prevent the fibers from flaking off over time, but, at the same time, should not be so tacky that the fibers are not dispersed in the composition.

The inventors envisaged including in the liquid fatty phase of cosmetic compositions comprising fibers, at least one heteropolymer, for example, at least one polyamide polymer, in an amount effective to disperse the fibers. In one embodiment, the fibers in the cosmetic compositions thus obtained were dispersed, and in a further embodiment, the compositions were glossy. In one embodiment, the compositions of the invention may prevent flaking. In another embodiment, the compositions of the invention may make it possible to obtain a cosmetic composition whose application can produce a glossy deposit and which may allow the fibers to adhere to eyelashes.

In one embodiment, the present invention provides methods for dispersing fibers in a cosmetic composition comprising: including in the composition at least one heteropolymer comprising a polymer skeleton which comprises at least one hydrocarbon-based repeating unit comprising at least one hetero atom in an amount effective to disperse the fibers.

In another embodiment, the present invention provides cosmetic compositions comprising (i) at least one heteropolymer comprising a polymer skeleton which comprises at least one hydrocarbon-based repeating unit comprising at least one hetero atom, (ii) fibers, and (iii) at least one polysaccharide resin, wherein the at least one heteropolymer is present in an amount effective to disperse the fibers.

In another embodiment, the present invention provides cosmetic compositions comprising (i) at least one heteropolymer comprising a polymer skeleton which comprises at least one hydrocarbon-based repeating unit comprising at least one hetero atom, (ii) fibers, and (iii) at least one copolymer film former chosen from di-block, tri-block, multi-block, and radial copolymers, wherein the at least one heteropolymer is present in an amount effective to disperse the fibers.

In yet another embodiment, the present invention provides methods of dispersing fibers in a cosmetic composition comprising including in said composition at least one heteropolymer and fibers, wherein the at least one heteropolymer is present in an amount effective to disperse the fibers.

Certain terms used herein are defined below:

"At least one" means one or more and thus includes individual components as well as mixtures/combinations.

"Alkyl group," as used herein, refers to substituted linear alkyl groups, unsubstituted linear alkyl groups, substituted branched alkyl groups, unsubstituted branched alkyl groups, substituted cyclic alkyl groups and unsubstituted cyclic alkyl groups, wherein the aforementioned alkyl groups comprise at least one carbon and may optionally further comprise at least one heteroatom intercalated in the alkyl chain.

"Alkenyl group," as used herein, refers to substituted linear alkenyl groups, unsubstituted linear alkenyl groups, substituted branched alkenyl groups, unsubstituted branched alkenyl groups, substituted cyclic alkenyl groups and unsubstituted cyclic alkenyl groups, wherein the aforementioned alkenyl groups comprise at least one carbon and at least one double bond, and may optionally further comprise at least one heteroatom intercalated in the alkenyl chain.

"Functionalized," as used herein, means comprising at least one functional group. Non-limiting examples of functional groups include hydroxyl groups, ether groups, oxyalkylene groups, polyoxyalkylene groups, carboxylic acid groups, amine groups, amide groups, halogen-containing groups, including fluoro groups and perfluoro groups, halogens, ester groups, siloxane groups and polysiloxane groups.

A "functionalized chain," as used herein, refers to, for example, an alkyl chain comprising at least one functional group chosen, for example, from those recited above. For example, in one embodiment, the hydrogen atoms of at least one alkyl chain may be substituted at least partially with fluorine atoms.

"Hydrocarbon-based oil," as used herein, refers to an oil comprising carbon and hydrogen atoms, optionally with at least one group chosen from hydroxyl groups, ester groups, carboxyl groups, and ether groups.

"Keratinous fibers," as used herein, includes hair, eyelashes, and eyebrows.

"Liquid fatty phase," as used herein, means a fatty phase which is liquid at room temperature (25□C) and atmospheric pressure (760 mmHg), and which comprises at least one fatty substance that is liquid at room temperature and atmospheric pressure, also referred to as an oil.

"Polymer," as used herein, means a compound comprising at least 2 repeating units.

It is to be understood that both the foregoing general description and the following detailed description are exemplary and explanatory only and are not restrictive of the invention as claimed. Reference will now be made in detail to exemplary embodiments of the present invention.

As described above, the present invention relates to compositions and methods for using compositions, e.g., for dispersing fibers and for making-up keratinous fibers, in particular human keratinous fibers, such as human eyelashes, comprising at least one heteropolymer and fibers, wherein the at least one heteropolymer is present in an amount effective to disperse the fibers. The composition may further comprise at least one liquid fatty phase.

The at least one heteropolymer of the present invention comprises a polymer skeleton comprising at least one hydrocarbon-based repeating unit comprising at least one hetero atom. In one embodiment, the at least one heteropolymer further comprises at least one chain chosen from:

(i) terminal fatty chains, optionally functionalized, chosen from alkyl chains, such as alkyl chains comprising at least four carbon atoms, and alkenyl chains, such as alkenyl chains comprising at least four carbon atoms, bonded to the polymer skeleton, such as a polyamide skeleton, via at least one linking group, and (ii) pendant fatty chains, optionally functionalized, chosen from alkyl chains, such as alkyl chains comprising at least four carbon atoms, and alkenyl chains, such as alkenyl chains comprising at least four carbon atoms, bonded to the polymer skeleton, such as a polyamide skeleton, via at least one linking group.

The at least one linking group, for example, may be chosen from direct bonds, urea groups, urethane groups, thiourethane groups, thioester groups, thioether groups, thiourea groups, ester groups, ether groups, and amine groups. In one embodiment, the at least one linking group is chosen from urea groups, ester groups, and amine groups. In another embodiment, the linking group is chosen from ester groups and amine groups.

In another embodiment, at least one of the terminal fatty chains and the pendant chains, optionally functionalized, comprises from 8 to 120 carbon atoms, such as in the form of alkyl and alkenyl chains, bonded to the polymer skeleton via at least one linking group. As is evident, the at least one heteropolymer may comprise both at least one pendant fatty chain and at least one terminal fatty chain as defined above.

In one embodiment, the at least one heteropolymer has a low weight-average molecular mass, such as less than 100,000.

The composition of the invention may be in the form of a paste, a cream, or a liquid. Further, the inventive composition may be a single emulsion (such as an oil-in-water or water-in-oil emulsion), a multiple emulsion (such as an oil-in-water-in-oil emulsion or a water-in-oil-in-water emulsion), or a rigid or soft gel comprising an oily continuous phase. For example, the liquid fatty phase may be the continuous phase of the composition. In one embodiment, the composition is in the form of a single emulsion. In a further embodiment, the composition is in the form of an oil-in-water emulsion.

Further, according to the present invention, the mascara may be a washable compositions, i.e., those that may be removed with water and/or soap (e.g., emulsions) or waterproof compositions (e.g., solvent-based compositions), depending on the additional compounds and the desired product.

Heteropolymer

In one embodiment, the at least one heteropolymer in the composition of the invention is a solid that is not deformable at room temperature (25° C.) and atmospheric pressure (760 mmHg). In another embodiment, the at least one heteropolymer is capable of structuring the composition without opacifying it.

As defined above, the at least one heteropolymer of the present invention comprises a polymer skeleton comprising at least one hydrocarbon-based repeating unit comprising at least one hetero atom. In one embodiment, the at least one heteropolymer further comprises at least one terminal fatty chain chosen from alkyl chains and alkenyl chains, such as chains comprising at least 4 atoms, and further such as chains comprising from 8 to 120 carbon atoms, bonded to the polymer skeleton via at least one linking group. The terminal fatty chain may, for example, be functionalized. The at least one heteropolymer may also further comprise at least one pendant fatty chain chosen from alkyl chains and alkenyl chains, such as chains comprising at least 4 atoms, and further such as chains comprising 8 to 120 carbon atoms, bonded to any carbon or hetero atom of the polymer skeleton via at least one linking group. The pendant fatty chain may, for example, be functionalized. The at least one heteropolymer may comprise both at least one pendant fatty chain and at least one terminal fatty chain as defined above, and one or both types of chains can be functionalized. Further, one or both types of chains may be linked directly to the polymer skeleton or via an ester function or a perfluoro group.

In one embodiment, the heteropolymer comprises at least two hydrocarbon-based repeating units. In another embodiment, the heteropolymer comprises at least three hydrocarbon-based repeating units. In yet another embodiment, the heteropolymer comprises at least three hydrocarbon-based repeating units, wherein the at least three repeating units are identical.

The hydrocarbon-based repeating unit may be chosen from saturated and unsaturated hydrocarbon-based repeating units, which, in turn, may be chosen from linear hydrocarbon-based repeating units, branched hydrocarbon-based repeating units and cyclic hydrocarbon-based repeating units. Non-limiting examples of the at least one hydrocarbon-based repeating unit include a repeating unit comprising from 2 to 80 carbon atoms and a repeating unit comprising from 2 to 60 carbon atoms. According to the present invention, the at least one hydrocarbon-based repeating unit may comprise at least one oxygen atom. Further, the at least one hydrocarbon-based repeating unit may comprise, for example, at least one hetero atom that is part of the polymer skeleton, i.e., not pendant. Non-limiting examples of the at least one hetero atom include nitrogen, sulphur, and phosphorus. In one embodiment, the at least one hetero atom is a nitrogen atom, such as a non-pendant nitrogen atom. In another embodiment, the at least one hydrocarbon-based repeating unit may comprise at least one hetero atom with the proviso that the at least one hetero atom is not nitrogen. In another embodiment, the at least one hetero atom is combined with at least one atom chosen from oxygen and carbon to form a hetero atom group. In one embodiment, the hetero atom group comprises a carbonyl group.

Non-limiting examples of the at least one repeating unit comprising at least one hetero atom include amide groups, carbamate groups, and urea groups. In one embodiment, the at least one repeating unit comprises amide groups forming a polyamide skeleton. In another embodiment, the at least one repeating unit comprises carbamate groups and/or urea groups forming a polyurethane skeleton, a polyurea skeleton and/or a polyurethane-polyurea skeleton. The pendant chains, for example, can be linked directly to at least one of the at least one hetero atom of the polymer skeleton. In yet another embodiment, the at least one hydrocarbon-based repeating unit may comprise at least one hetero atom group with the proviso that the at least one hetero atom group is not an amide group. In one embodiment, the polymer skeleton comprises at least one repeating unit chosen from silicone units and oxyalkylene units, the at least one repeating unit being between the hydrocarbon-based repeating units.

In one embodiment, the compositions of the present invention comprise at least one heteropolymer comprising nitrogen atoms, such as amide units, urea units, and carbamate units and at least one polar oil.

In another embodiment, in the at least one heteropolymer, the percentage of the total number of fatty chains ranges from 40% to 98% relative to the total number of repeating units and fatty chains, and as a further example, from 50% to 95%. In a further embodiment wherein the polymer skeleton is a polyamide skeleton, in the at least one heteropolymer, the percentage of the total number of fatty chains ranges from 40% to 98% relative to the total number of all amide units and fatty chains, and as a further example, from 50% to 95%.

In a further embodiment, the nature and proportion of the at least one hydrocarbon-based repeating unit comprising at least one hetero atom depends on the nature of a liquid fatty phase of the composition and is, for example, similar to the nature of the fatty phase. For example, not to be limited as to theory, the more polar the hydrocarbon-based repeating units comprising a hetero atom, and in higher proportion, which corresponds to the presence of several hetero atoms, the greater the affinity of the at least one heteropolymer to polar oils. Conversely, the more non-polar, or even apolar, and lesser in proportion the hydrocarbon-based repeating units comprising a hetero atom, the greater the affinity of the polymer for apolar oils.

In another embodiment, the at least one liquid fatty phase comprising with at least one heteropolymer, wherein the at least one heteropolymer is a polyamide comprising a polymer skeleton comprising at least one amide repeating unit and optionally at least one pendant fatty chain and/or at least one terminal chain that are optionally functionalized and comprise from 8 to 120 carbon atoms, bonded to at least one of the amide repeating units via at least one linking group. The liquid fatty phase further contains fibers. The at least one heteropolymer is present in the inventive composition in an amount effective to disperse the fibers.

When the heteropolymer has amide repeating units, the pendant fatty chains may be linked to at least one of the nitrogen atoms in the amide repeating units.

The heteropolymer, for example the polyamide polymer, may have a weight-average molecular mass of less than 100,000, such as less than 50,000. In another embodiment, the weight-average molecular mass may range from 1000 to 30,000, such as from 2000 to 20,000, further such as from 2000 to 10,000.

As discussed, the at least one heteropolymer may, for example, be chosen from polyamide polymers. A polyamide polymer may comprise, for example, a polymer skeleton which comprises at least one amide repeating unit, i.e., a polyamide skeleton. In one embodiment, the polyamide skeleton may further comprise at least one terminal fatty chain chosen from alkyl chains, for example, alkyl chains comprising at least four carbon atoms, and alkenyl chains, for example, alkenyl chains comprising at least four carbon atoms, bonded to the at least one polyamide skeleton via at least one linking group, and/or at least one pendant fatty chain chosen from alkyl chains, for example, alkyl chains comprising at least four carbon atoms, and alkenyl chains, for example, alkenyl chains comprising at least four carbon atoms, bonded to the at least one polyamide skeleton via at least one linking group. In one embodiment, the polyamide skeleton may comprise at least one terminal fatty chain chosen from fatty chains comprising 8 to 120 carbon atoms, such as, for example, 12 to 68 carbon atoms, bonded to the at least one polyamide skeleton via at least one linking group and/or at least one pendant fatty chain chosen from fatty chains comprising 8 to 120 carbon atoms, such as, for example, 12 to 68 carbon atoms, bonded to the at least one polyamide skeleton via at least one linking group, such as bonded to any carbon or nitrogen of the polyamide skeleton via the at least one linking group. In one embodiment, the at least one linking group is chosen from direct bonds, urea groups, urethane groups, thiourea groups, thiourethane groups, thioether groups, thioester groups, ester groups, ether groups, and amine groups. The bond is, for example, an ester bond. In one embodiment, these polymers comprise a fatty chain at each end of the polymer skeleton, such as the polyamide skeleton.

In one embodiment, due to the presence of at least one chain, the polyamide polymers may be readily soluble in oils (i.e., water-immiscible liquid compounds) and thus may give macroscopically homogeneous compositions even with a high content (at least 25%) of the polyamide polymers, unlike certain polymers of the prior art that do not contain such alkyl chains or alkenyl chains at the end of the polyamide skeleton. As defined herein, a composition is soluble if it has a solubility of greater than 0.01 g per 100 ml of solution at 25° C.

In a further embodiment, the polyamide polymers can be chosen from polymers resulting from at least one polycondensation reaction between at least one acid chosen from dicarboxylic acids comprising at least 32 carbon atoms, such as 32 to 44 carbon atoms, and at least one amine chosen from diamines comprising at least 2 carbon atoms, such as from 2 to 36 carbon atoms, and triamines comprising at least 2 carbon atoms, such as from 2 to 36 carbon atoms. The dicarboxylic acids can, for example, be chosen from dimers of at least one fatty acid comprising at least 16 carbon atoms, such as oleic acid, linoleic acid and linolenic acid. The at least one amine can, for example, be chosen from diamines, such as ethylenediamine, hexylenediamine, hexamethylenediamine, phenylenediamine and triamines, such as ethylenetriamine.

The polyamide polymers may also be chosen from polymers comprising at least one terminal carboxylic acid group. The at least one terminal carboxylic acid group can, for example, be esterified with at least one alcohol chosen from monoalcohols comprising at least 4 carbon atoms. For example, the at least one alcohol can be chosen from monoalcohols comprising from 10 to 36 carbon atoms. In a further embodiment, the monoalcohols can comprise from 12 to 24 carbon atoms, such as from 16 to 24 carbon atoms, and for example 18 carbon atoms.

In one embodiment, the at least one polyamide polymer may be chosen from those described in U.S. Pat. No. 5,783,657, the disclosure of which is incorporated herein by reference, which are polyamide polymers of formula (I):

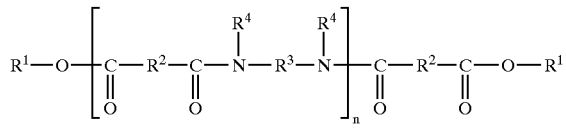

(I)

in which:

n is an integer which represents the number of amide units such that the number of ester groups present in the at least one polyamide polymer ranges from 10% to 50% of the total number of all the ester groups and all the amide groups comprised in the at least one polyamide polymer;

$R^1$, which are identical or different, are each chosen from alkyl groups comprising at least 4 carbon atoms and alkenyl groups comprising at least 4 carbon atoms. In one embodiment, the alkyl group comprises from 4 to 24 carbon atoms and the alkenyl group comprises from 4 to 24 carbon atoms;

$R^2$, which are identical or different, are each chosen from $C_4$ to $C_{42}$ hydrocarbon-based groups with the proviso that at least 50% of all $R^2$ are chosen from $C_{30}$ to $C_{42}$ hydrocarbon-based groups;

$R^3$, which are identical or different, are each chosen from organic groups comprising atoms chosen from carbon atoms, hydrogen atoms, oxygen atoms and nitrogen atoms with the proviso that $R^3$ comprises at least 2 carbon atoms; and $R^4$, which are identical or different, are each chosen from hydrogen atoms, $C_1$ to $C_{10}$ alkyl groups, and direct bonds to at least one group chosen from $R^3$ and another $R^4$ such that when the at least one group is chosen from another $R^4$, the nitrogen atom to which both $R^3$ and $R^4$ are bonded forms part of a heterocyclic structure defined in part by $R^4$—N—$R^3$, with the proviso that at least 50% of all $R^4$ are chosen from hydrogen atoms.

In the polymer of formula (I), the terminal fatty chains that are optionally functionalized for the purposes of the invention are terminal chains linked to the last hetero atom, in this case nitrogen, of the polyamide skeleton.

In one embodiment, the ester groups of formula (I), which form part of the terminal and/or pendant fatty chains for the purposes of the invention, are present in an amount ranging from 15% to 40% of the total number of ester and amide groups, such as from 20% to 35%.

In formula (I), in one embodiment, n may be an integer ranging from 1 to 5, for example an integer ranging from 3 to 5. In the present invention, $R^1$, which are identical or different, can, for example, each be chosen from $C_{12}$ to $C_{22}$ alkyl groups, such as from $C_{16}$ to $C_{22}$ alkyl groups.

In the present invention, $R^2$, which are identical or different, can, for example, each be chosen from $C_{10}$ to $C_{42}$ hydrocarbon-based, e.g., alkylene groups. At least 50% of all $R^2$, for example at least 75% of all $R^2$, which are identical or different, can, for example, each be chosen from groups comprising from 30 to 42 carbon atoms. In the two aforementioned embodiments, the remaining $R^2$, which are identical or different, can, for example, each be chosen from $C_4$ to $C_{18}$ groups, such as $C_4$ to $C_{12}$ groups.

$R^3$, which can be identical or different, can, for example, each be chosen from $C_2$ to $C_{36}$ hydrocarbon-based groups and polyoxyalkylene groups. In another example, $R^3$, which can be identical or different, can each, for example, be chosen from $C_2$ to $C_{12}$ hydrocarbon-based groups. In another embodiment, $R^4$, which can be identical or different, can each be chosen from hydrogen atoms. As used herein, hydrocarbon-based groups may be chosen from linear saturated hydrocarbon-based groups, linear unsaturated hydrocarbon-based groups, cyclic saturated hydrocarbon-based groups, cyclic unsaturated hydrocarbon-based groups, branched saturated hydrocarbon-based groups, and branched saturated hydrocarbon-based groups. The hydrocarbon-based groups can also be chosen from aliphatic hydrocarbon-based groups and aromatic hydrocarbon-based groups. In one example, the hydrocarbon-based groups are chosen from aliphatic hydrocarbon-based groups. The alkyl groups may be chosen from linear saturated alkyl groups, linear unsaturated alkyl groups, cyclic saturated alkyl groups, cyclic unsaturated alkyl groups, branched saturated alkyl groups, and branched unsaturated alkyl groups. The alkylene groups may be chosen from linear saturated alkylene groups, linear unsaturated alkylene groups, cyclic saturated alkylene groups, cyclic unsaturated alkylene groups, branched saturated alkylene groups, and branched unsaturated alkylene groups.

In general, the pendant fatty chains and terminal fatty chains, which may be identical or different, may be chosen from linear saturated fatty chains, linear unsaturated fatty chains, cyclic saturated fatty chains, cyclic unsaturated fatty chains, branched saturated fatty chains, and branched unsaturated fatty chains. The pendant fatty chains and terminal fatty chains can also be chosen from aliphatic fatty chains and aromatic fatty chains. In one example, the pendant fatty chains and terminal fatty chains are chosen from aliphatic fatty chains.

In one embodiment of the present invention, structuring of the liquid fatty phase may be obtained with the aid of at least one heteropolymer, such as the at least one polymer of formula (I). The at least one polyamide polymer of formula (I) may, for example, be in the form of a mixture of polymers, and this mixture may also comprise a compound of formula (I) wherein n is equal to zero, i.e., a diester.

Non-limiting examples of the at least one polyamide polymer which may be used in the composition according to the present invention include the commercial products sold by Arizona Chemical under the names Uniclear 80 and Uniclear 100. These are sold, respectively, in the form of an 80% (in terms of active material) gel in a mineral oil and a 100% (in terms of active material) gel. These polymers have a softening point ranging from 88□C to 94□C, and may be mixtures of copolymers derived from monomers of (i) $C_{36}$ diacids and (ii) ethylenediamine, and have a weight-average molecular mass of about 6000. Terminal ester groups result from esterification of the remaining acid end groups with at least one alcohol chosen from cetyl alcohol and stearyl alcohol. A mixture of cetyl and stearyl alcohols is sometimes called cetylstearyl alcohol.

Other non-limiting examples of the at least one polyamide polymer which may be used in the compositions according to the present invention include polyamide polymers resulting from the condensation of at least one aliphatic dicarboxylic acid and at least one diamine, the carbonyl groups and amine groups being condensed to form an amide bond. In one embodiment, these polymers contain more than two carbonyl groups and more than two amine groups. Examples of these polyamide polymers are those sold under the brand name Versamid by the companies General Mills Inc. and Henkel Corp. (Versamid 930, 744 or 1655) or by the company Olin Mathieson Chemical Corp. under the brand name Onamid, in particular Onamid S or C. These polymers have a weight-average molecular mass ranging from 6000 to 9000. For further information regarding these polyamides, reference may be made to U.S. Pat. Nos. 3,645,705 and 3,148,125, the disclosures of which are hereby incorporated by reference. In one embodiment, Versamid 930 or 744 may be used.

Other examples of polyamides include those sold by the company Arizona Chemical under the names Uni-Rez (2658, 2931, 2970, 2621, 2613, 2624, 2665, 1554, 2623 and 2662) and the product sold under the name Macromelt 6212 by the company Henkel. For further information regarding these polyamides, reference may be made to U.S. Pat. No. 5,500,209, the disclosure of which is hereby incorporated by reference. Such polyamides display high melt viscosity characteristics. Macromelt 6212, for example, has a high melt viscosity at 190° C. of 30–40 poise (as measured by a Brookfield Viscometer, Model RVF #3 spindle, 20 RPM).

In a further embodiment, the at least one polyamide polymer may be chosen from polyamide resins from vegetable sources. Polyamide resins from vegetable sources may be chosen from, for example, the polyamide resins of U.S. Pat. Nos. 5,783,657 and 5,998,570, the disclosures of which are herein incorporated by reference.

The at least one heteropolymer in the compositions of the invention may have a softening point greater than 50□C, such as from 65□C to 190□C, and further such as from 70□C to 130□C, and even further such as from 80□C to 105□C. This softening point may be lower than that of structuring polymers used in the art which may facilitate the use of the at least one heteropolymer of the present invention and may limit the degradation of the liquid fatty phase. These polymers may be non waxy polymers.

In one embodiment, the at least one heteropolymer in the composition according to the invention corresponds to the polyamide polymers of formula (I). Due to fatty chain(s), these polymers may be readily soluble in oils and thus lead to compositions that are macroscopically homogeneous even with a high content (at least 25%) of at least one heteropolymer, unlike polymers not comprising a fatty chain.

According to the present invention, the at least one heteropolymer is present in the inventive composition in an amount effective to disperse the fibers. Dispersion of fibers can be evaluated by at least the following methods. First, the fibers are "dispersed," as used herein, if, when a sample of the composition comprising the fibers is placed between 2 microscope slides, there are no agglomerates visible to the naked eye. Agglomeration is a well known phenomenon in the art, thus one of ordinary skill in the art should be able to readily determine whether the fibers are present in the composition in the form of agglomerates.

A second possible test is the evaluation of glossiness of the composition. As previously discussed, it is well known that as the dispersion of the fibers increases, so too does the gloss. A cosmetic composition is provided with gloss, as used herein, when there is a measurable increase in the gloss of the composition upon addition of the at least one heteropolymer to the cosmetic composition. The gloss of a composition may, for example, be measured and evaluated using a gloss meter. Gloss meters are commonly used in the nail polish art, and measure the amount of light reflected from the surface or film of interest. The gloss may be quantified, for example, as a % reflectance. In one embodiment, the gloss of a cosmetic composition comprising the at least one heteropolymer is greater than the gloss of the composition prior to addition of the at least one heteropolymer. Thus, gloss meter readings of the composition can be measured to determine the gloss, and thus the dispersion, of a composition comprising fibers. The composition may be proportionally more glossy the higher the degree of dispersion of the fibers.

For example, the at least one heteropolymer may be present in the composition in an amount generally ranging from 0.1% to 60% by weight relative to the total weight of the composition, such as for example 1% to 40%, and further, for example, from 2 to 30%. In a further embodiment the at least one heteropolymer may be present in the composition in an amount ranging, for example, from 5% to 25% by weight relative to the total weight of the composition.

In another embodiment of the invention, the present invention is drawn to a composition comprising at least one heteropolymer which comprises a polymer skeleton comprising at least one hydrocarbon-based repeating unit comprising at least one hetero atom, wherein the at least one heteropolymer further comprises at least one terminal fatty chain, optionally functionalized, chosen from alkyl chains and alkenyl chains, such as alkyl chains comprising at least four carbon atoms and alkenyl chains comprising at least four carbon atoms, and further such as alkyl chains comprising from 8 to 120 carbon atoms and alkenyl chains comprising from 8 to 120 carbon atoms, bonded to the polymer skeleton via at least one linking group chosen from amide groups, urea groups, and ester groups, wherein when the at least one linking group is chosen from ester groups, the at least one terminal fatty chain is chosen from branched alkyl groups. The at least one heteropolymer may also comprise at least one pendant fatty chain, optionally functionalized, chosen from alkyl chains and alkenyl chains, such as alkyl comprising at least four carbon atoms and alkenyl chains comprising at least four carbon atoms, and further such as alkyl chains comprising from 8 to 120 carbon atoms and alkenyl chains comprising from 8 to 120 carbon atoms, bonded to any carbon or hetero atom of the polymer skeleton via at least one linking group chosen from amide groups, urea groups, and ester groups, wherein when the at least one linking group is chosen from ester groups, the at least one terminal fatty chain is chosen from branched alkyl groups. The at least one heteropolymer may comprise both at least one pendant fatty chain and at least one terminal fatty chain as defined above in this paragraph.

Fibers

The fibers useful in the present invention may be chosen from natural and synthetic fibers. Natural fibers include, but are not limited to, cotton, silk, wool, and other keratin fibers. Synthetic fibers include, but are not limited to, polyester, rayon, nylon and other polyamide fibers. In one embodiment, the fibers of the invention are chosen from elastomeric fibers, such as those described in EP 1172 078 A2, more specifically paragraphs 16–24, the disclosure of which is herein incorporated by reference.

Fibers may, for example, be present in the composition in an amount ranging from 0.5% to 10% relative to the total weight of the composition. In a further embodiment, the fibers are present in an amount ranging from 1% to 5% relative to the total weight of the composition. In one embodiment, the fibers may, for example, have an average length ranging from 0.5 mm to 4.0 mm, such as from 1.5 mm to 2.5 mm.

Polysaccharide Resin

In one embodiment, the present invention provides cosmetic compositions comprising (i) at least one heteropolymer comprising a polymer skeleton which comprises at least one hydrocarbon-based repeating unit comprising at least one hetero atom, (ii) fibers, and (iii) at least one polysaccharide resin, wherein the at least one heteropolymer is present in an amount effective to disperse the fibers.

In one embodiment, the at least one polysaccharide resin of the present invention comprises numerous hydroxyl groups and hydrophobic groups. The at least one polysaccharide resin can be in the form of colloidal suspensions of fine, highly modified particles such as starch particles. The fine particles may vary in size, and may, for example, include particles with a diameter of 10 microns or less.

Non-limiting examples of the at least one polysaccharide resin of the present invention include the polysaccharide resins available from KAMA, International Corp., Duluth, Ga. For example, polysaccharide resin KM13 is a highly modified, colloidal suspension in water of finely divided starch particles with a diameter of less than 10 microns. KM13 is a co-reactive resin which will form hydrogen bonds with other resins. This polysaccharide resin contains numerous hydroxyl groups which contribute to the wetting of pigments in aqueous systems and hydrophobic groups that permit acceptance in solvent based systems without pigment flocculation or flotation.

Polysaccharide resins are generally water soluble and therefore a polysaccharide film former may be formulated by dissolving the at least one polysaccharide resin in an aqueous system. In another embodiment, the polysaccharide resin may be added to other solvent based systems by dispersing into the solvent system a polysaccharide resin that has been previously dissolved in water.

If the composition of the present invention is in the form of an emulsion, the at least one polysaccharide resin may be contained in either the aqueous phase or in the oil phase or both. In one embodiment, the at least one polysaccharide resin is in the aqueous phase.

Depending on the application, the amount of the at least one polysaccharide resin in the inventive composition may vary considerably. One of skill in the art will be able to determine routinely the preferred concentration of the at least one polysaccharide resin depending on the application and the properties desired. In one embodiment, the compositions of the present invention comprise at least one polysaccharide resin, such as KM13, in an amount generally ranging from 1% to 50% by weight relative to the weight of the total composition. In another embodiment, the at least one polysaccharide resin is present in an amount ranging from 5% to 40% by weight. For example, for cosmetic foundations, the at least one polysaccharide resin may be present in the inventive compositions in an amount generally ranging from 1% to 50% by weight, such as from 1% to 20% by weight. For eyeliner formulations, the at least one polysaccharide resin may be present in the inventive compositions in an amount generally ranging from 1% to 30% by weight, such as from 2% to 20% by weight. For mascara formulations, the at least one polysaccharide resin may be present in an amount generally ranging from 0.5% to 50% by weight, such as from 1% to 20% by weight.

Copolymer Film Former

In one embodiment, the present invention provides cosmetic compositions comprising (i) at least one heteropolymer comprising a polymer skeleton which comprises at least one hydrocarbon-based repeating unit comprising at least one hetero atom, (ii) fibers, and (iii) at least one copolymer film former chosen from di-block, tri-block, multi-block, and radial copolymers, wherein the at least one heteropolymer is present in an amount effective to disperse the fibers.

In one embodiment, the di-block, tri-block, multi-block and/or radial or star block copolymer film formers used in the invention comprise at least two thermodynamically incompatible segments. A di-block is usually defined as A-B type or a hard segment (A) followed by a soft segment (B) in sequence. A tri-block is usually defined as a A-B-A type copolymer or a ratio of one hard, one soft, and one hard segment. Multiblock or radial or star copolymer film formers usually contain any combination of hard and soft segments, provided that there are both hard and soft characteristics. A non-limiting example of a hard block copolymer segment is styrene, while non-limiting examples of soft block copolymer segments are ethylene, propylene, and butylene or combinations thereof.

In another embodiment, the copolymer film former of the present invention is chosen from the class of Kraton® rubbers (Shell Chemical Company) or from similar gelling agents. In a further embodiment, the copolymer film former comprises Kraton® rubbers that are present in a gel in amounts from about 10 to about 20% concentration by weight. Kraton® rubbers are thermoplastic elastomers in which the polymer chains comprise a tri-block, di-block, or radial or star block configuration or numerous mixtures thereof. The Kraton® tri-block rubbers have polystyrene segments on each end of a rubber segment, while the Kraton® di-block rubbers have a polystyrene segment attached to a rubber segment. The Kraton® radial or star configuration, in a further preferred embodiment, may be a four-point or other multipoint star made of rubber with a polystyrene segment attached to each end of a rubber segment. The configuration of each of the Kraton® rubbers form separate polystyrene and rubber domains.

Each molecule of Kraton® rubber is said to comprise block segments of styrene monomer units and rubber monomer and/or co-monomer units. The most common structure for the Kraton® triblock copolymer is the linear A-B-A block type styrene-butadiene-styrene, styrene-isoprene-styrene, or styrene-ethylenebutylene-styrene. The Kraton® di-block may be AB block type such as styrene-ethylenepropylene, styrene-ethylenebutylene, styrene-butadiene, and styrene-isoprene. The Kraton® rubber configuration is well known in the art and any block copolymer film former with a similar configuration is within the practice of the invention.

Other non-limiting examples of block copolymer film formers include those comprising a styrene/butylene/ethylene/styrene copolymer (tri-block), an ethylene/propylene/styrene copolymer (radial or star block) or a mixture or blend of the two. (Some manufacturers refer to block copolymers as hydrogenated block copolymers, e.g. hydrogenated styrene/butylene/ethylene/styrene copolymer (tri-block) or hydrogenated ethylene/propylene/styrene copolymer (radial or star block), all of which are within the scope of the invention.) Specific non-limiting examples include Versagel M5960, or Versagel M5970, all of which are available from Penreco of Houston Tex. and block copolymers available from Brooks Industries, such as Gel Base.

The block copolymer film former may, for example, be formulated by dissolving the block copolymer in a hydrocarbon solvent. Hydrocarbons useful in the practice of the invention include but are not limited to mineral oils, mineral solvents, mineral spirits, petroleum, waxes, synthetic hydrocarbons, animal oils, vegetable oils, and mixtures of various hydrogen carbons. In one embodiment, the block copolymer film former is formulated by dissolving the block copolymer in isododecane and/or a light paraffinic solvent. In another embodiment, the block copolymer film former may be formulated by dissolving the block copolymer in a non-hydrocarbon solvent such as amyl acetate, butyl acetate, isobutyl acetate, ethyl acetate, propyl acetate and isopropyl acetate.

The solvent and solubility conditions for formulating a block copolymer film former from a block copolymer will be chosen by a person skilled in the art in order to prepare a composition which has the desired properties. One of ordinary skill in the art will be able to determine the solubility parameters and choose a solvent based on the block copolymer chosen for the envisaged application. More information regarding solubility parameters and solvents useful in the processing of specific block copolymers is available from the various manufacturers of block copolymers, e.g. Shell Chemical Company. Additional discussions of polymer solubility parameter concepts are presented in: *Encyclopedia of Polymer Science and Technology*, Vol. 3, Interscience, New York (1965) and *Encyclopedia of Chemical Technology*, Supp. Vol., Interscience, New York (1971), the disclosures of which are hereby incorporated by reference.

In one embodiment, the at least one block copolymer film former of the present invention is water insoluble, can be processed at room temperature, offer excellent adherence to the skin, and are tack free. The at least one copolymer film former may, for example, be present in the outer phase of any cosmetic formulation and at high concentrations. Additionally, the at least one copolymer film former may, for example, be compatible with the other raw materials of that phase.

Depending on the application, the concentration of the at least one block copolymer film former may vary considerably. One of skill in the art will be able to determine routinely the desired concentration of the at least one block copolymer film former depending on the application and the properties desired.

Coloring Agent

The compositions of the present invention, in one embodiment, may further comprise at least one coloring agent. Non-limiting examples of the at least one coloring agent include lipophilic dyes, hydrophilic dyes, traditional pigments, and nacres usually used in cosmetic or dermatological compositions, and mixtures thereof. Further, the at least one coloring agent may have any shape, such as, for example, spheroidal, oval, platelet, irregular, and mixtures thereof. The at least one coloring agent, if present, can generally be present in an amount ranging from 0.01% to 50% relative to the total weight of the composition, for example from 0.5% to 40%, and, as a further example, from 5% to 30%, if it is present.

The liposoluble dyes include, for example, Sudan Red, D&C Red 17, D&C Green 6, -carotene, soybean oil, Sudan Brown, D&C Yellow 11, D&C Violet 2, D&C Orange 5, quinoline yellow and annatto. The liposoluble dyes can be present in an amount ranging from 0.1% to 20% relative to the total weight of the composition, for example from 0.1% to 6% (if present). The water-soluble dyes are, for example, beetroot juice or methylene blue, and can be present in an amount up to 6% relative to the total weight of the composition.

The pigments may be white pigments, colored pigments, inorganic pigments, organic pigments, coated pigments, uncoated pigments, pigments having a micron size and pigments not having a micron size. Among the inorganic pigments which may be mentioned are titanium dioxide, optionally surface-treated, zirconium oxide, zinc oxide, cerium oxide, iron oxide, chromium oxide, manganese violet, ultramarine blue, chromium hydrate and ferric blue. Among the organic pigments which may be mentioned are carbon black, pigments of D&C type, lakes based on cochineal carmine, lakes based on barium, lakes based on strontium, lakes based on calcium, and lakes based on aluminium. The pigment(s) can be present in an amount ranging from 0.1% to 50%, for example from 0.5% to 40%, and, as a further example, from 2% to 30% relative to the total weight of the composition, if they are present.

The nacreous pigments may, for example, be chosen from white nacreous pigments such as mica coated with titanium and mica coated with bismuth oxychloride, colored nacreous pigments such as titanium mica with iron oxides, titanium mica with, for example, ferric blue and/or chromium oxide, titanium mica with an organic pigment of the type mentioned above, as well as nacreous pigments based on bismuth oxychloride, interferential pigments, and goniochromatic pigments. They can be present in an amount ranging from 0.1% to 20% relative to the total weight of the composition, for example from 0.1% to 15%, if they are present.

Liquid Fatty Phase

The at least one liquid fatty phase, in one embodiment, may comprise at least one oil. The at least one oil, for example, may be chosen from polar oils and apolar oils including hydrocarbon-based liquid oils and oily liquids at room temperature. In one embodiment, the compositions of the invention comprise at least one heteropolymer, fibers, and at least one polar oil. The polar oils of the invention, for example, may be added to the apolar oils, the apolar oils acting in particular as co-solvents for the polar oils.

According to the invention, structuring of the at least one liquid fatty phase may be obtained with the aid of at least one heteropolymer, such as the polymer of formula (I). In general, the polymers of formula (I) may be in the form of mixtures of polymers, these mixtures also possibly comprising a synthetic product corresponding to a compound of formula (I) in which n is 0, i.e., a diester.

The liquid fatty phase of the composition may comprise more than 30%, for example, more than 40%, of liquid oil(s) having a chemical nature close to the chemical nature of the skeleton (hydrocarbon or silicone based) of the heteropolymer, and for example from 50% to 100%. In one embodiment, the liquid fatty phase comprising, as the at least one heteropolymer, a polyamide-type skeleton, or polyurea, or polyurethane, or polyurea-urethane-type skeleton comprises a high quantity, i.e., greater than 30%, for example greater than 40% relative to the total weight of the liquid fatty phase, such as from 50% to 100%, of at least one apolar, such as hydrocarbon-based, oil.

For a liquid fatty phase comprising, as the at least one heteropolymer, a polymer comprising a partially silicone-based skeleton, this fatty phase may contain more than 30%, for example, more than 40%, relative to the total weight of the liquid fatty phase and, for example, from 50% to 100%, of at least one silicone-based liquid oil, relative to the total weight of the liquid fatty phase.

For a liquid fatty phase comprising, as the at least one heteropolymer, an apolar polymer of the hydrocarbon-based type, this fatty phase may contain more than 30%, for example more than 40% by weight, and, as a further example, from 50% to 100% by weight, of at least one liquid apolar, such as hydrocarbon-based, oil, relative to the total weight of the liquid fatty phase.

For example, the at least one polar oil useful in the invention may be chosen from:

hydrocarbon-based plant oils with a high content of triglycerides comprising fatty acid esters of glycerol in which the fatty acids may have varied chain lengths from $C_4$ to $C_{24}$, these chains possibly being chosen from linear saturated chains, linear unsaturated chains, branched saturated chains, and branched unsaturated chains; these oils can be chosen from, for example, wheat germ oil, corn oil, sunflower oil, karite butter, castor oil, sweet almond oil, macadamia oil, apricot oil, soybean oil, cotton oil, alfalfa oil, poppy oil, pumpkin oil, sesame oil, marrow oil, rapeseed oil, avocado oil, hazelnut oil, grape seed oil, blackcurrant seed oil, evening primrose oil, millet oil, barley oil, quinoa oil, olive oil, rye oil, safflower oil, candlenut oil, passion flower oil and musk rose oil; or alternatively caprylic/capric acid triglycerides such as those sold by Stearineries Dubois and those sold under the names Miglyol 810, 812 and 818 by Dynamit Nobel;

synthetic oils of formula $R_5COOR_6$ and synthetic esters of formula $R_5COOR_6$, in which $R_5$ is chosen from linear fatty acid residues comprising from 1 to 40 carbon atoms and branched fatty acid residues comprising from 1 to 40 carbon atoms, and $R_6$ is chosen from, for example, hydrocarbon-based chains comprising from 1 to 40 carbon atoms, on condition that $R_5+R_6 \geq 10$, such as, for example, purcellin oil (cetostearyl octanoate), isononyl isononanoate, $C_{12}$–$C_{15}$ alkyl benzoates, isopropyl myristate, 2-ethylhexyl palmitate, isostearyl isostearate and alkyl octanoates, polyalkyl octanoates, decanoates, ricinoleates; hydroxylated esters such as isostearyl lactate and diisostearyl malate; and pentaerythritol esters;

synthetic ethers comprising from 10 to 40 carbon atoms;

$C_8$ to $C_{26}$ fatty alcohols such as oleyl alcohol; and $C_8$ to $C_{26}$ fatty acids such as oleic acid, linolenic acid, and linoleic acid.

The at least one apolar oil according to the invention is chosen from, for example, silicone oils chosen from linear volatile polydimethylsiloxanes (PDMSs) that are liquid at room temperature, linear non-volatile polydimethylsiloxanes that are liquid at room temperature, cyclic volatile polydimethylsiloxanes that are liquid at room temperature, and cyclic non-volatile polydimethylsiloxanes that are liquid at room temperature; polydimethylsiloxanes comprising at least one group chosen from alkyl groups and alkoxy groups, wherein the alkyl groups and alkoxy groups are chosen from pendant groups and groups at the end of the silicone chain, and further wherein the alkyl groups and alkoxy groups each comprise from 2 to 24 carbon atoms; phenylsilicones such as phenyl trimethicones, phenyl dimethicones, phenyl trimethylsiloxy diphenylsiloxanes, diphenyl dimethicones, diphenyl methyldiphenyl trisiloxanes, and 2-phenylethyl trimethylsiloxysilicates; hydrocarbons chosen from linear and branched, volatile and non-volatile hydrocarbons of synthetic and mineral origin, such as volatile liquid paraffins (such as isoparaffins and isododecanes) and non-volatile liquid paraffins, and derivatives thereof, liquid petrolatum, liquid lanolin, polydecenes, hydrogenated polyisobutene, and squalane; and mixtures thereof. The structured oils, for example those structured with polyamides such as those of formula (I) or with polyurethanes, polyureas, polyureaurethanes, in accordance with the invention, may be, in one embodiment, apolar oils, such as an oil or a mixture of hydrocarbon oils chosen from those of mineral and synthetic origin, chosen from hydrocarbons such as alkanes such as Parleam®, isoparaffins including isododecane, and squalane, and mixtures thereof. These oils may, in one embodiment, be combined with at least one phenylsilicone oil.

The liquid fatty phase, in one embodiment, contains at least one non-volatile oil chosen from, for example, hydrocarbon-based oils of mineral, plant and synthetic origin, synthetic esters, synthetic ethers, silicone oils and mixtures thereof.

In practice, the total liquid fatty phase can be, for example, present in an amount ranging from 1% to 99% by weight relative to the total weight of the composition, for example from 5% to 95.5%, from 10% to 80%, or from 20% to 75%.

For the purposes of the invention, the expression "volatile solvent or oil" means any non-aqueous medium capable of evaporating on contact with the skin or the lips in less than one hour at room temperature and atmospheric pressure. The volatile solvent(s) of the invention is(are) organic solvents, such as volatile cosmetic oils that are liquid at room temperature, having a non-zero vapor pressure, at room temperature and atmospheric pressure, ranging in particular from $10^{-2}$ mmHg to 300 mmHg and, for example, greater than 0.3 mmHg. The expression "non-volatile oil" means an oil which remains on the skin or the lips at room temperature and atmospheric pressure for at least several hours, such as those having a vapor pressure of less than $10^{-2}$ mmHg.

According to the invention, these volatile solvents may impart at least one desirable characteristic to the inventive composition, such as, for example, staying power and long wear properties. The solvents can be chosen from hydrocarbon-based solvents, silicone solvents optionally comprising alkyl and/or alkoxy groups that are pendant and/or at the end of a silicone chain, and a mixture of these solvents.

The volatile oil(s), in one embodiment, is present in an amount ranging up to 95.5% relative to the total weight of the composition, such as from 2% to 75%, and, as a further example, from 10% to 45%. This amount will be adapted by a person skilled in the art according to the desired staying power and long wearing properties.

The at least one liquid fatty phase of the compositions of the invention may further comprises a dispersion of lipid vesicles. The compositions of the invention may also, for example, be in the form of a fluid anhydrous gel, a rigid anhydrous gel, a fluid simple emulsion, a fluid multiple emulsion, a rigid simple emulsion or a rigid multiple emulsion. The simple emulsion or multiple emulsion may comprise a continuous phase chosen from an aqueous phase optionally comprising dispersed lipid vesicles and/or oil droplets and a fatty phase optionally comprising dispersed lipid vesicles and/or water droplets. In one embodiment, the composition has a continuous oily phase or fatty phase and is more specifically an anhydrous composition, for example, a stick or dish form. An anhydrous composition is one that has less than 10% water by weight, such as, for example, less than 5% by weight.

Further, the present invention, in another embodiment, relates to a make-up and/or care and/or treatment composition for keratinous fibers (i) at least one heteropolymer comprising a polymer skeleton which comprises at least one hydrocarbon-based repeating unit comprising at least one hetero atom; and (ii) fibers, wherein the at least one heteropolymer is present in an amount effective to disperse the fibers.

The present invention also relates, in one embodiment, to a treatment, care or make-up composition for keratinous fibers comprising at least one heteropolymer comprising a polymer skeleton comprising at least one hydrocarbon-based repeating unit comprising at least one hetero atom, and fibers, wherein the at least one heteropolymer is present in an amount effective to disperse the fibers.

Further, another embodiment of the present invention provides a composition comprising (i) at least one heteropolymer comprising a polymer skeleton comprising at least one hydrocarbon-based repeating unit comprising at least one hetero atom, wherein the at least one heteropolymer further comprises at least one terminal fatty chain, optionally functionalized, chosen from alkyl chains and alkenyl chains, wherein the at least one terminal fatty chain is bonded to the polymer skeleton via at least one linking group chosen from amide groups, urea groups, and ester groups, wherein when the at least one linking group is chosen from ester groups, the at least one terminal fatty chain is chosen from branched alkyl groups, and (ii) fibers, wherein the at least one heteropolymer is present in an amount effective to disperse the fibers. In another embodiment, the at least one heteropolymer may also comprise at least one pendant fatty chain, optionally functionalized, chosen from alkyl chains and alkenyl chains, wherein the at least one pendant fatty chain is bonded to the polymer skeleton via bonded to any carbon or hetero atom of the polymer skeleton via at least one linking group chosen from amide groups, urea groups, and ester groups, wherein when the at least one linking group is chosen from ester groups, the at least one pendant fatty chain is chosen from branched alkyl groups.

Further, an embodiment of the present invention relates to a method for care, make up, or treatment of keratin fibers comprising applying to the keratin fibers a cosmetic composition comprising (i) at least one heteropolymer comprising a polymer skeleton which comprises at least one hydrocarbon-based repeating unit comprising at least one hetero atom; and (ii) fibers, wherein the at least one heteropolymer is present in an amount effective to disperse the fibers.

Additionally, an embodiment of the present invention relates to a method for making a cosmetic composition in the form of a physiologically acceptable composition comprising including in the composition (i) at least one heteropolymer comprising a polymer skeleton which comprises at least one hydrocarbon-based repeating unit comprising at least one hetero atom; and (ii) fibers, wherein the at least one heteropolymer is present in an amount effective to disperse the fibers.

Additionally, an embodiment of the present invention is drawn to a composition comprising at least one liquid fatty phase which comprises (i) at least one heteropolymer comprising a polymer skeleton which comprises at least one hydrocarbon-based repeating unit comprising at least one hetero atom; and at least one terminal fatty chain chosen from alkyl chains and alkenyl chains, wherein the at least one terminal fatty chain is bonded to the polymer skeleton via at least one linking group; and (ii) fibers, wherein the at least one heteropolymer is present in an amount effective to disperse the fibers.

The present invention also provides, in one embodiment, a method for providing at least one of gloss, intense color and water resistance to a cosmetic composition, comprising including in the cosmetic composition (i) at least one heteropolymer comprising a polymer skeleton which comprises at least one hydrocarbon-based repeating unit comprising at least one hetero atom; and (ii) fibers, wherein the at least one heteropolymer is present in an amount effective to disperse the fibers.

Another embodiment of the present invention relates to a method for dispersing fibers in a cosmetic composition comprising including the cosmetic composition (i) at least one heteropolymer comprising a polymer skeleton which comprises at least one hydrocarbon-based repeating unit comprising at least one hetero atom in an amount effective to disperse the fibers.

Film Formers

The composition according to the invention may also contain at least one film former different from the at least one block copolymer film former and different from the at least one polysaccharide resin. Non-limiting examples of the at least one film former include those listed at pages 1744 to 1747 of the CTFA *International Cosmetic Ingredient Dictionary and Handbook*, $8^{th}$ Ed. (2000).

Waxes

The composition can optionally contain at least one wax. The at least one wax may impart at least one desired characteristic to the inventive compositions. For the purposes of the present invention, a wax is a lipophilic fatty compound that is solid at room temperature (25°C) and atmospheric pressure (760 mmHg), which undergoes a reversible solid/liquid change of state, having a melting point of greater than 40°C, for example greater than 55°C and which may be up to 200°C, and having an anisotropic crystal organization in the solid state. By bringing the wax to its melting point, it is possible to make it miscible with oils and to form a microscopically homogeneous mixture, but on returning the temperature of the mixture to room temperature, recrystallization of the wax in the oils of the mixture is obtained. The waxes may be present in an amount ranging up to 20% relative to the total weight of the composition, for example from 0.1% to 15%, and, as a further example, from 1% to 5%.

For the purposes of the invention, the waxes are those generally used in cosmetics and dermatology; such as those of natural origin, for instance beeswax, carnauba wax, candelilla wax, ouricury wax, Japan wax, cork fibre wax, sugar cane wax, paraffin wax, lignite wax, microcrystalline waxes, lanolin wax, montan wax, ozokerites and hydrogenated oils such as hydrogenated jojoba oil as well as waxes of synthetic origin, for instance polyethylene waxes derived from the polymerization of ethylene, waxes obtained by Fischer-Tropsch synthesis, fatty acid esters and glycerides that are solid at 40°C, for example, at above 55°C, silicone waxes such as alkyl- and alkoxy-poly(di)methylsiloxanes and/or poly(di)methylsiloxane esters that are solid at 40°C and, for example, at above 55°C.

According to the invention, the melting point values correspond to the melting peak measured by the differential scanning calorimetry method with a temperature rise of 5 or 10°C/min.

Other Ingredients

The composition of the present invention, in one embodiment, may comprise a physiologically acceptable medium. The composition may also further comprise at least one suitable additive commonly used in the field concerned chosen from anionic surfactants, nonionic surfactants, cationic surfactants, amphoteric surfactants, zwitterionic surfactants, plasticizers, antioxidants, essential oils, preserving agents, fragrances, neutralizing agents, liposoluble polymers, and cosmetically active agents and dermatological active agents such as, for example, emollients, moisturizers, vitamins, essential fatty acids and sunscreens. The at least one additive is generally present in a concentration ranging from 0% to 20% by weight of the total weight of the composition, such as from 0% to 10%.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. The following examples are intended to illustrate the invention without limiting the scope as a result.

EXAMPLES

Example 1

Solvent Based Composition

The following composition was prepared and the dispersion of the fibers therein was evaluated.

TABLE 1

Solvent based composition.

| Component | Weight Percent |
|---|---|
| Isododecane | 35.22 |
| Sorbitan Sesquioleate | 0.25 |
| Pigment | 6.00 |
| Disteardimonium hectorite | 5.80 |
| Rice starch | 1.00 |
| Isododecane and styrene ethylene/butylenes/styrene triblock polymer and styrene ethylene propylene radial block polymer (Versagel MD 870) | 5.00 |
| Rayon flock fiber | 2.00 |
| Nylon -66 | 2.00 |
| Waxes | 20.00 |
| Polyamide polymer (Uniclear) | 2.00 |
| Alkyl stearate/VAC copolymer | 2.40 |
| Polyvinyl Laurate | 1.00 |
| Hydrogenated Polyisobutene | 8.00 |
| Propylene carbonate | 1.82 |
| C8-9 isoparaffin/Isopar E | 8.50 |
| Phenonip | 0.01 |

A drop of the above inventive composition was placed between a microscope slide. No agglomerates were visible to the naked eye, thus indicating dispersion of the fibers in the composition.

Example 2

Emulsion Based Composition

The following composition was prepared and the dispersion of the fibers therein was evaluated.

TABLE 1

Emulsion based composition.

| Component | Weight Percent |
|---|---|
| Waxes | 5.30 |
| Glyceryl Stearate | 3.00 |
| Steric Acid | 3.00 |
| PVP/Eicosene copolymer | 1.50 |
| Polysynlane SV | 10.00 |
| Uniclear 100 | 1.50 |
| Methylparaben | 0.20 |
| Disodium EDTA | 0.20 |
| Hydroxyethyl cellulose | 0.20 |
| Butylene glycol | 2.00 |
| Methylparaben | 0.20 |
| KAMA KM 13 (hydroxylated corn starch) | 0.95 |
| Triethanolamine | 1.50 |
| Simethicone | 0.10 |
| Sorbitan Sesquioleate | 0.20 |
| PVP/VA copolymer | 1.00 |
| Pigment | 6.00 |
| Rayon fiber | 3.00 |
| Acrylates Copolymer | 10.00 |
| Liquipar Optima | 1.10 |
| Sodium Dehydroacetate | 0.20 |
| Denatured Alcohol | 5.00 |
| Water | q.s. to 100 |

A drop of the above inventive composition was placed between a microscope slide. No agglomerates were visible to the naked eye, thus indicating dispersion of the fibers in the composition.

What is claimed is:

1. A composition comprising:
   (i) at least one heteropolymer chosen from polyamide polymers of formula (I):

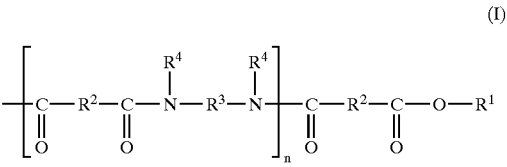

(I)

in which:
   n is an integer which represents the number of amide units such that the number of ester groups present in said at least one polyamide polymer ranges from 10% to 50% of the total number of all ester groups and all amide groups comprised in said at least one polyamide polymer;
   $R^1$, which are identical or different, are each chosen from alkyl groups comprising at least 4 carbon atoms and alkenyl groups comprising at least 4 carbon atoms;
   $R^2$, which are identical or different, are each chosen from $C_4$ to $C_{42}$ hydrocarbon-based groups with the proviso that at least 50% of all $R^2$ are chosen from $C_{30}$ to $C_{42}$ hydrocarbon-based groups;
   $R^3$, which are identical or different, are each chosen from organic groups comprising atoms chosen from carbon atoms, hydrogen atoms, oxygen atoms and nitrogen atoms, with the proviso that $R^3$ comprises at least 2 carbon atoms; and
   $R^4$, which are identical or different, are each chosen from hydrogen atoms, $C_1$ to $C_{10}$ alkyl groups and a direct bond to at least one group chosen from $R^3$ and another $R^4$ such that when said at least one group is chosen from another $R^4$, the nitrogen atom to which both $R^3$ and $R^4$ are bonded forms part of a heterocyclic structure defined in part by $R^4$—N—$R^3$, with the proviso that at least 50% of all $R^4$ are chosen from hydrogen atoms;

(ii) fibers; and (iii) at least one compound chosen from at least one polysaccharide resin and at least one copolymer film former chosen from di-block, tri-block, multi-block, and radial copolymers, wherein said at least one heteropolymer is present in an amount effective to disperse said fibers.

2. The composition according to claim 1, wherein in said formula (I), n is an integer ranging from 1 to 5.

3. The composition according to claim 1, further comprising at least one liquid fatty phase.

4. The composition according to claim 3, wherein said at least one liquid fatty phase of the composition comprises at least one oil.

5. The composition according to claim 4, wherein said at least one oil is chosen from at least one polar oil and at least one apolar oil.

6. The composition according to claim 5, wherein said at least one polar oil is chosen from:

hydrocarbon-based plant oils with a high content of triglycerides comprising fatty acid esters of glycerol in which the fatty acids comprise chains having from 4 to 24 carbon atoms, said chains optionally being chosen from linear and branched, and saturated and unsaturated chains;

synthetic oils or esters of formula $R_5COOR_6$ in which $R_5$ is chosen from linear and branched fatty acid residues comprising from 1 to 40 carbon atoms and $R_5+R_6 \geq 10$;

synthetic ethers comprising from 10 to 40 carbon atoms;

$C_8$ to $C_{26}$ fatty alcohols; and $C_8$ to $C_{26}$ fatty acids.

7. The composition according to claim 5, wherein said at least one apolar oil is chosen from:

silicone oils chosen from volatile and non-volatile, linear and cyclic polydimethylsiloxanes that are liquid at room temperature;

polydimethylsiloxanes comprising alkyl or alkoxy groups which are pendant and/or at the end of the silicone chain, the groups each comprising from 2 to 24 carbon atoms;

phenylsilicones; and hydrocarbons chosen from linear and branched, volatile and non-volatile hydrocarbons of synthetic and mineral origin.

8. The composition according to claim 3, wherein said at least one liquid fatty phase comprises at least one non-volatile oil.

9. The composition according to claim 8, wherein said at least one non-volatile oil is chosen from hydrocarbon-based oils of mineral, plant and synthetic origin, synthetic esters and ethers, and silicone oils.

10. The composition according to claim 9, wherein said at least one liquid fatty phase is present in an amount ranging from 1% to 99% by weight relative to the total weight of the composition.

11. The composition according to claim 3, wherein said at least one liquid fatty phase comprises at least one volatile solvent chosen from hydrocarbon-based solvents and silicone solvents optionally comprising alkyl or alkoxy groups that are pendant or at the end of a silicone chain.

12. The composition according to claim 1, wherein said fibers are chosen from natural and synthetic fibers.

13. The composition according to claim 12, wherein said natural fibers are chosen from cotton, silk, wool, and other keratin fibers.

14. The composition according to claim 12, wherein said synthetic fibers are chosen from polyester, rayon, nylon, and other polyamide fibers.

15. The composition according to claim 12, wherein said fibers have an average length ranging from 0.5 mm to 4.0 mm.

16. The composition according to claim 15, wherein said fibers have an average length ranging from 1.5 mm to 2.5 mm.

17. The composition according to claim 1, wherein said fibers are present in the composition in an amount ranging from 0.5% to 10% relative to the total weight of the composition.

18. The composition according to claim 1, further comprising at least one film former different from said at least one compound chosen from at least one polysaccharide resin and at least one copolymer film former chosen from di-block, tri-block, multi-block, and radial copolymers.

19. The composition according to claim 1, wherein the composition is in a form chosen from a fluid gel, rigid gel, fluid single emulsion, rigid single emulsion, fluid multiple emulsion, and rigid multiple emulsion.

20. A composition comprising:

(i) at least one heteropolymer chosen from polyamide polymers of formula (I):

$$R^1-O-\left[\begin{array}{c} C-R^2-C-N-R^3-N \\ \parallel \quad \parallel \quad | \quad \quad | \\ O \quad O \quad R^4 \quad R^4 \end{array}\right]_n C-R^2-C-O-R^1$$

in which:

n is an integer which represents the number of amide units such that the number of ester groups present in said at least one polyamide polymer ranges from 10% to 50% of the total number of all ester groups and all amide groups comprised in said at least one polyamide polymer;

$R^1$, which are identical or different, are each chosen from alkyl groups comprising at least 4 carbon atoms and alkenyl groups comprising at least 4 carbon atoms;

$R^2$, which are identical or different, are each chosen from $C_4$ to $C_{42}$ hydrocarbon-based groups with the proviso that at least 50% of all $R^2$ are chosen from $C_{30}$ to $C_{42}$ hydrocarbon-based groups;

$R^3$, which are identical or different, are each chosen from organic groups comprising atoms chosen from carbon atoms, hydrogen atoms, oxygen atoms and nitrogen atoms, with the proviso that $R^3$ at least 2 carbon atoms; and $R^4$, which are identical or different, are each chosen from hydrogen atoms, $C_1$ to $C_{10}$ alkyl groups and a direct bond to at least one group chosen from $R^3$ and another $R^4$ such that when said at least one group is chosen from another $R^4$, the nitrogen atom to which both $R^3$ and $R^4$ are bonded forms part of a heterocyclic structure defined in part by $R^4$—N—$R^3$, with the proviso that at least 50% of all $R^4$ are chosen from hydrogen;

(ii) fibers, (iii) at least one polysaccharide resin, and
(iv) at least one copolymer film former chosen from di-block, tri-block, multi-block, and radial copolymers,
wherein said at least one heteropolymer is present in an amount effective to disperse said fibers.

21. A method for dispersing fibers in a cosmetic composition which comprises fibers comprising including in said cosmetic composition at least one heteropolymer chosen from polyamide polymers of formula (I):

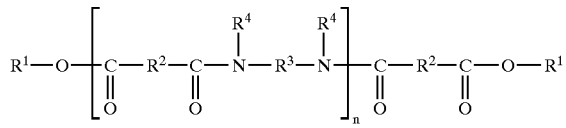

(I)

in which:
- n is an integer which represents the number of amide units such that the number of ester groups present in said at least one polyamide polymer ranges from 10% to 50% of the total number of all ester groups and all amide groups comprised in said at least one polyamide polymer;
- $R^1$, which are identical or different, are each chosen from alkyl groups comprising with at least 4 carbon atoms and alkenyl groups comprising at least 4 carbon atoms;
- $R^2$, which are identical or different, are each chosen from $C_4$ to $C_{42}$ hydrocarbon-based groups with the proviso that at least 50% of all $R^2$ are chosen from $C_{30}$ to $C_{42}$ hydrocarbon-based groups;
- $R^3$, which are identical or different, are each chosen from organic groups comprising atoms chosen from carbon atoms, hydrogen atoms, oxygen atoms and nitrogen atoms, with the proviso that $R^3$ comprises at least 2 carbon atoms; and
- $R^4$, which are identical or different, are each chosen from hydrogen atoms, and $C_1$ to $C_{10}$ alkyl groups and a direct bond to at least one group chosen from $R^3$ and another $R^4$ such that when said at least one group is chosen from another $R^4$, the nitrogen atom to which both $R^3$ and $R^4$ are bonded forms part of a heterocyclic structure defined in part by $R^4$—N—$R^3$, with the proviso that at least 50% of all $R^4$ are chosen from hydrogen;

in an amount effective to disperse said fibers.

22. The method according to claim 21, wherein said cosmetic composition further comprises at least one liquid fatty phase.

23. The method according to claim 21, wherein said cosmetic composition further comprises at least one compound chosen from at least one polysaccharide resin and at least one copolymer film former chosen from di-block, tri-block, multi-block, and radial copolymers.

24. The composition according to claim 1, wherein the at least one heteropolymer is chosen from ethylenediamine/stearyl dimer tallate copolymer.

25. The composition according to claim 20, wherein the at least one heteropolymer is chosen from ethylenediamine/stearyl dimer tallate copolymer.

26. The method according to claim 21, wherein the at least one heteropolymer is chosen from ethylenediamine/stearyl dimer tallate copolymer.

27. The composition according to claim 1, wherein the at least one heteropolymer is chosen from ethylenediamine/stearyl dimer dilinoleate copolymer.

28. The composition according to claim 20, wherein the at least one heteropolymer is chosen from ethylenediamine/stearyl dimer dilinoleate copolymer.

29. The method according to claim 21, wherein the at least one heteropolymer is chosen from ethylenediamine/stearyl dimer dilinoleate copolymer.

* * * * *

UNITED STATES PATENT AND TRADEMARK OFFICE
CERTIFICATE OF CORRECTION

PATENT NO. : 7,008,629 B2 Page 1 of 1
DATED : March 7, 2006
INVENTOR(S) : Mohamed Kanji It is certified that error appears in the above-identified patent and that said Letters Patent is hereby corrected as shown below:

<u>Column 22,</u>
Line 57, "$R^3$ at" should read -- $R^3$ comprises at --.

Signed and Sealed this

Thirteenth Day of June, 2006

JON W. DUDAS
*Director of the United States Patent and Trademark Office*